(12) United States Patent
Kitching et al.

(10) Patent No.: US 10,098,709 B1
(45) Date of Patent: Oct. 16, 2018

(54) CONSTRAINED OPTIMIZATION OF ORTHODONTIC BRACKET PLACEMENT AND ARCHWIRE SMOOTHING

(71) Applicant: ORMCO CORPORATION, Orange, CA (US)

(72) Inventors: Ian D. Kitching, Highland, CA (US); Evan Yifeng, Pasadena, CA (US); Pawan Deshmukh, Maharashtra (IN)

(73) Assignee: Ormco Corporation, Orange, CA (US)

( * ) Notice: Subject to any disclaimer, the term of this patent is extended or adjusted under 35 U.S.C. 154(b) by 312 days.

(21) Appl. No.: 14/747,138

(22) Filed: Jun. 23, 2015

Related U.S. Application Data

(60) Provisional application No. 62/016,584, filed on Jun. 24, 2014.

(51) Int. Cl.
| | |
|---|---|
| *A61C 3/00* | (2006.01) |
| *A61C 7/00* | (2006.01) |
| *A61C 9/00* | (2006.01) |
| *A61C 7/14* | (2006.01) |
| *G05B 19/4097* | (2006.01) |

(52) U.S. Cl.
CPC ............ *A61C 7/002* (2013.01); *A61C 7/146* (2013.01); *A61C 9/0053* (2013.01); *G05B 19/4097* (2013.01)

(58) Field of Classification Search
CPC ....... A61C 7/002; A61C 7/146; A61C 9/0046; A61C 9/0053; A61C 2007/004; G05B 19/4097

USPC .......................................................... 433/29
See application file for complete search history.

(56) References Cited

U.S. PATENT DOCUMENTS

| | | | |
|---|---|---|---|
| 5,027,281 | A | 6/1991 | Rekow et al. |
| 5,431,562 | A | 7/1995 | Andreiko et al. |
| 6,616,444 | B2 | 9/2003 | Andreiko et al. |
| 6,733,289 | B2 | 5/2004 | Manemann et al. |
| 6,928,733 | B2 | 8/2005 | Rubbert et al. |
| 7,296,996 | B2 | 11/2007 | Sachdeva et al. |
| 7,751,925 | B2 | 7/2010 | Rubbert et al. |
| 7,837,464 | B2 | 11/2010 | Marshall |
| 7,840,373 | B2 | 11/2010 | Culp et al. |
| 8,105,080 | B2 | 1/2012 | Chishti et al. |
| 8,194,067 | B2 | 6/2012 | Raby et al. |
| 8,200,462 | B2 | 6/2012 | Marshall et al. |

FOREIGN PATENT DOCUMENTS

EP          0420059 A1      4/1991

*Primary Examiner* — Mallika D Fairchild
(74) *Attorney, Agent, or Firm* — Wood Herron & Evans LLP

(57) ABSTRACT

A method and system for generated an optimized placement of orthodontic brackets on a set of teeth with the goal of smoothing the orthodontic archwire associated with the brackets. The optimized placement takes into account at least one constraint, such as minimum height of the brackets or minimum distance from the center of the tooth. Generating the optimized placement may take the form of iteratively re-positioned the brackets on the underlying teeth to derive the most optimal placement within the bounds of the given constraints.

22 Claims, 25 Drawing Sheets

CONSTRAINED OPTIMIZATION OF ORTHODONTIC BRACKET PLACEMENT AND ARCHWIRE SMOOTHING

TECHNICAL FIELD

The disclosure relates to a method, system, and computer readable storage medium for the constrained optimization of orthodontic bracket placement and archwire smoothing.

CROSS REFERENCE TO RELATED APPLICATION

This application is related to U.S. Provisional Patent Application Ser. No. 62/016,584 filed Jun. 24, 2014, which claims benefit therefrom, entitled "Constrained Optimization of Orthodontic Bracket Placement and Archwire Smoothing," which is hereby incorporated by reference in its entirety.

BACKGROUND OF THE INVENTION

Orthodontics is a specialty of dentistry that is concerned with improvement of the general appearance of a patient's teeth and also the correction of malocclusions, crookedness and other flaws of the teeth. Orthodontic braces are devices that are placed on a patient's teeth by a dental practitioner. In an orthodontic brace, wires interact with brackets to move teeth to a desired position over time. Often, such orthodontic braces are periodically adjusted by the dental practitioner to help align and straighten the teeth. Treatment by the dental practitioner may help in repositioning the teeth to correct flaws and improve the general appearance of the patient.

The current process of custom orthodontic bracket placement and archwire smoothing, in a digital environment, may involve manual operations by a trained technician. In certain environments, a Computer Aided Design/Manufacturing (CAD/CAM) software may provide various interactive manipulation and diagnostic tools, where the interactive tools help the technician in making design decisions, and in meeting the quality standards. This manual process is often labor-intensive and time-consuming in view of the complicated nature of manufacturing and the aesthetic constraints in custom brackets. Furthermore, a significant amount of training and experience is required to master the necessary skills. Additionally, even for skillful technicians, the design outcome varies noticeably from person to person.

SUMMARY OF THE PREFERRED EMBODIMENTS

Provided are a method, system, and article of manufacture in which a computational device generates a design and a placement of a plurality of brackets to satisfy one or more manufacturing constraints and one or more design constraints. The design and the placement of the plurality of brackets are modified to allow a smoothed archwire to pass through slots of the plurality of brackets.

In certain embodiments, the manufacturing constraints include restrictions on spatial clearances in the facial-lingual direction, and restrictions on allowed rotations about an occlusal-gingival axis.

In further embodiments, the design constraints include centering of the plurality of brackets on teeth, smoothness of the archwire, and shortness of a bracket.

In yet further embodiments, the generating and modifying further comprises, generating an initial design and placement of the plurality of brackets on teeth, where the initial design and placement violates at least one manufacturing constraint. Modified designs and placements of the plurality of brackets are iteratively generated to satisfy the violated manufacturing constraint while continuing to satisfy other manufacturing constraints and the design constraints.

In additional embodiments, the generating and modifying further comprises designing shortest possible brackets.

In further embodiments, the generating and modifying further comprises centering the plurality of brackets on teeth.

In certain embodiments, the generating and modifying further comprises using optimization techniques to iteratively smooth the archwire, where a smoothed archwire does not have kinks.

In certain embodiments, the system may comprise a computational device or an intra-oral imaging system.

BRIEF DESCRIPTION OF THE DRAWINGS

Referring now to the drawings in which like reference numbers represent corresponding parts throughout.

DETAILED DESCRIPTION

In the following description, reference is made to the accompanying drawings which form a part hereof and which illustrate several embodiments. It is understood that other embodiments may be utilized and structural and operational changes may be made.

Placement Design of Custom Orthodontic Brackets

The placement design of custom orthodontic brackets in a digital environment may include utilizing three dimensional scanned image of a patient's teeth, and eventually generating machining codes for the manufacturing of custom-designed brackets. Over the years, many solutions have been proposed for the design of such brackets. While many of these solutions enhance certain aspects of the interactive placement design process, for example, via the use of planes as visual guides, or via an unified simulation environment, the solutions fail to systematically optimize the bracket placement in an automated manner such that that multiple design objectives may be achieved simultaneously.

Certain embodiments provide mechanisms for automatically computing the placement of orthodontic brackets such that multiple objectives are achieved simultaneously. Such objectives include the satisfaction of all constraints, smoothing archwires, and generating minimum bracket heights. Certain embodiments employ optimization techniques to treat the entire bracket assembly as a system of many design parameters, as opposed to manual interactive adjustments by human technicians, which can only focus on one local aspect at a time. As a result the embodiments allow for a much faster and reliable convergence to the ideal placement design for brackets.

Furthermore, since the human factor is removed as much as possible from the process, the design result is more predictable, and provides greater conformance to a given orthodontic treatment setup. This makes it much easier for the designer to achieve quality and reliability in the design process.

Certain embodiments reduce the amount of manual intervention in the placement design of orthodontic brackets. In addition, the embodiments provide visual suggestions on further improvement in the setup of an expected orthodontic treatment outcome. The efficiency, quality, and reliability of the process are greatly enhanced.

EXEMPLARY EMBODIMENTS

Figure 1:
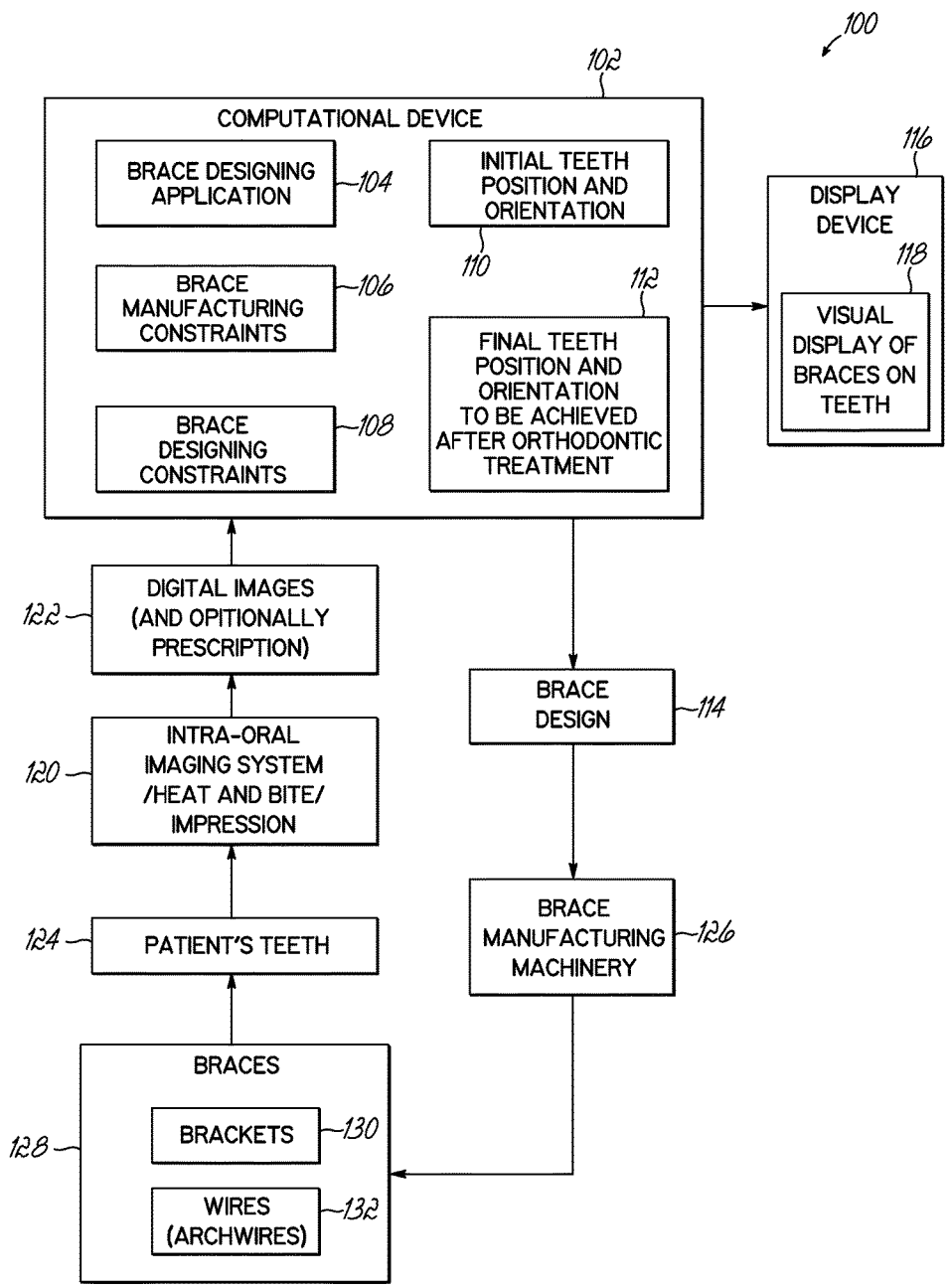
FIG. 1 illustrates a block diagram of a computing, design, manufacturing, and usage environment for placing braces on a patient's teeth, in accordance with certain embodiments.

FIG. 1 illustrates a block diagram of a computing, design, manufacturing, and usage environment 100 for placing braces on a patient's teeth, in accordance with certain embodiments.

The computing, design, manufacturing, and usage environment 100 includes at least a computational device 102. The computational device 102 may include any suitable computational device known in the art, such as a personal computer, a server, a mainframe computer, a telephony device, a hand held computer, a blade computer, a client computer, an embedded computing device, etc. The computational device 102 may be coupled to a network (not shown) such as a local area network, the Internet, an intranet, etc.

The computational device 102 may include a brace designing application 104, where the brace designing application 104 designs braces based on brace manufacturing constraints 106 and brace designing constraints 108 stored in the computational device 102.

The computational device 102 may also optionally store an initial position and orientation 110 of a patient's teeth, and the teeth position and orientation to be achieved after orthodontic treatment 112. The brace designing application 104 generates a brace design 114, such that the manufacturing constraints 106 and the designing constraints 108 are satisfied, and the designed braces when manufactured or machined and placed on a patient's teeth are able to move the patient's teeth from the initial teeth position and orientations 110 to the final teeth position and orientation 112 after orthodontic treatment.

In certain embodiments, a display device 116 is coupled to the computational device 102, where the brace designing application 104 is able to provide a visual display 118 of the designed braces as they would appear on the teeth of a patient. Controls provided with the visual display 118 may allow a technician to adjust parameters associated with the design of the braces.

In certain embodiments, a dental practitioner may use an intra-oral imaging system 120 to generate digital images 122 of a patient's teeth 124, where the digital images 122 along with an optional prescription for brace design may be received by the computational device 102 for designing the braces. The intra-oral imaging system 120 may include components like a memory, and a processor coupled to the memory, along with a display, camera, etc., for acquiring images, performing various operations and displaying images. In certain embodiments, instead of using an intra-oral imaging system 120, the dental practitioner may use a heat and bite mechanism or an impression mechanism to generate representations of the patient's teeth to send to the computational device 102. In the heat and bite mechanism a patient bites into a shape set polymer to generate an impression of the patient's teeth. Digital images 122 corresponding to the heat and bite impression may be generated, for being processed by the computational device 102. In certain alternative embodiments digital images 122 corresponding to the impressions obtained via the impression mechanism may be generated for processing by the computational device 102.

While in FIG. 1, the computational device 102 and the display device 116 have been shown outside the intra-oral imaging system 120, in certain alternative embodiments the operations performed by the computational device 102 and the display device 116 may be performed by the intra-oral imaging system 120.

The brace design 114 generated by the computational device 102 is used by a brace manufacturing/machining machinery 126 to manufacture braces 128. The dental practitioner may place the braces 128 on the patient's teeth 124. The braces 128 may be comprised of brackets 130 and wires 132, where the wires 132 may also be referred to as archwires. The dental practitioner may periodically adjust the wires 132 and this may over a course of time move the patient's teeth 124 to a desired final position and orientation 112. Once the desired final position and orientation 112 has been achieved for the patient's teeth, the braces 128 may be removed.

Therefore, FIG. 1 illustrates certain embodiments in which a brace designing application 104 generates a brace design 114 that satisfies various manufacturing constraints 106 and design constraints 108.

Figure 2:
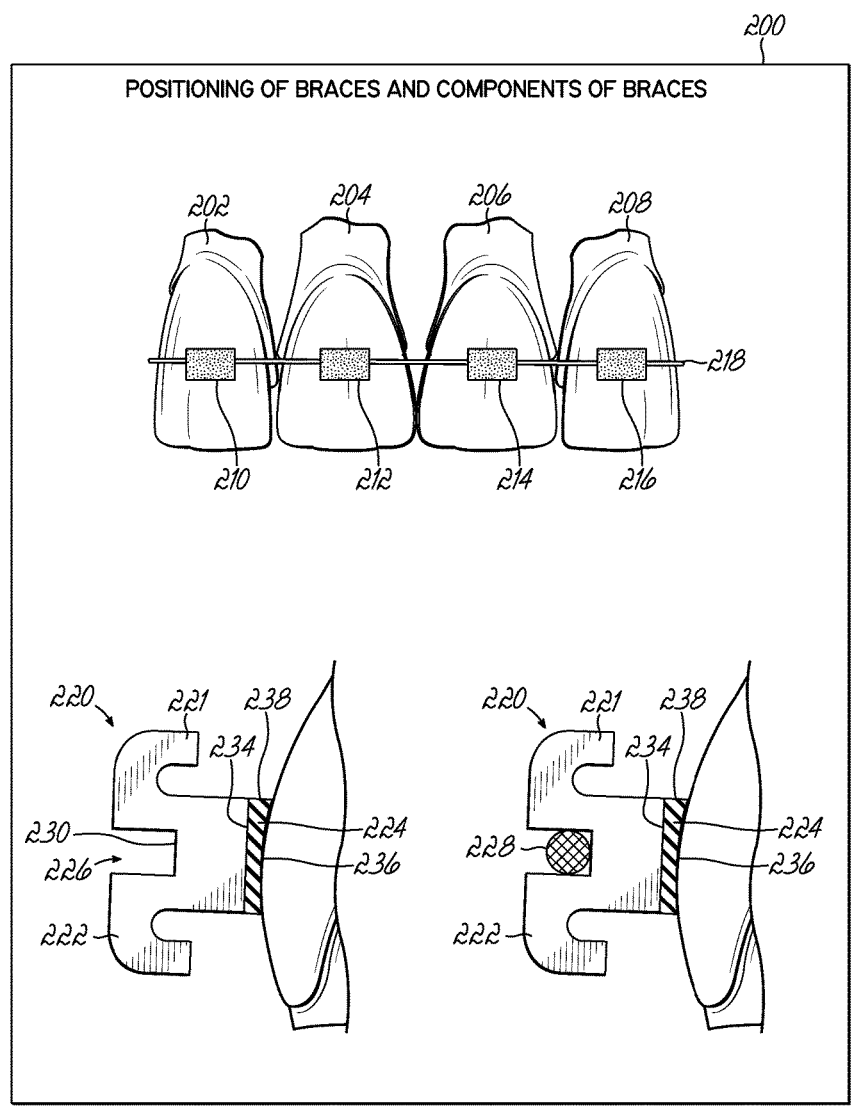
FIG. 2 illustrates a block diagram that shows exemplary positioning of braces and various components of braces, in accordance with certain embodiments.

FIG. 2 illustrates a block diagram 200 that shows exemplary positioning of braces and various components of braces, in accordance with certain embodiments.

In FIG. 2 a plurality of teeth 202, 204, 206, 208 are shown. On each tooth there is a bracket and exemplary brackets 210, 212, 214, 216 that are bonded to the plurality of teeth 202, 204, 206, 208 are shown. An archwire 218 that goes through the brackets is also shown. The archwire 218 may be adjusted periodically by a dental practitioner to move the teeth and also to keep the brackets in place.

FIG. 2 also shows the cross sectional view 220 of a bracket. A bracket is comprised of a bracket body 222 and a bracket pad 224 that are made to adhere to each other. The bracket body 222 has a pair of wings 221 and holes or channels referred to as slots through which the archwire can run through. An exemplary slot is 226 is shown. The slots 226 may of course be designed differently, in other embodiments. For example, the slots 226 may be a cylinder shaped groove that is completely enclosed by the bracket body 222 in alternative embodiments. Slot 226 includes an inner face 230. The bracket pad 224 includes a front surface 234, a rear surface 236, and a top surface 238. Additionally, an archwire 228 passing through the slot 226 is also shown in FIG. 2. It should be noted that FIG. 2 shows stock brackets. In stock brackets, only a limited selection of stock bracket bodies and stock pads are manufactured and they are then machined to fit each other in accordance with the bracket design 114 generated by the computational device 102.

Figure 3:
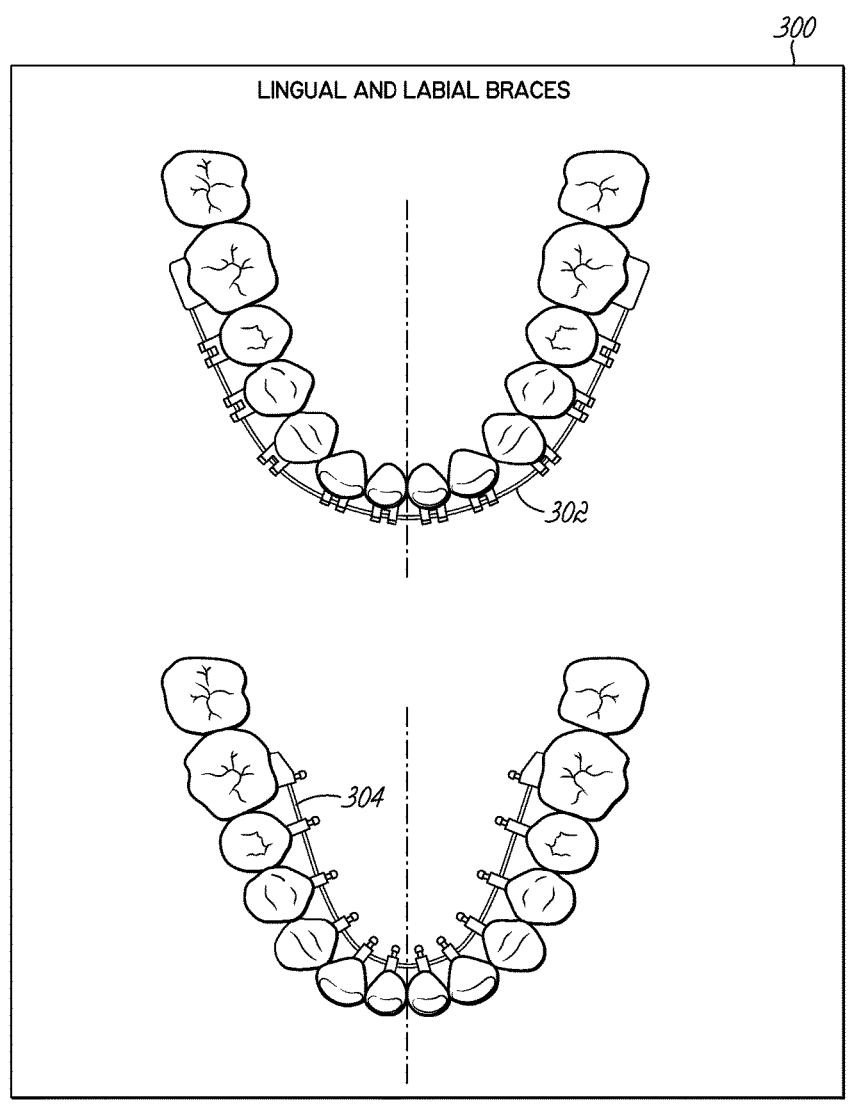
FIG. 3 illustrates a block diagram that shows lingual and labial braces, in accordance with certain embodiments.

FIG. 3 illustrates a block diagram 300 that shows a set of lingual braces 304 and a set of labial braces 302 on a dental arch, in accordance with certain embodiments. The labial braces 302 are placed on the teeth towards the side of the lips, and the lingual braces 304 are placed on the teeth towards the side of the tongue. Either lingual braces 304 or labial braces 302 may be designed in certain embodiments by the brace designing application 104.

Figure 4:
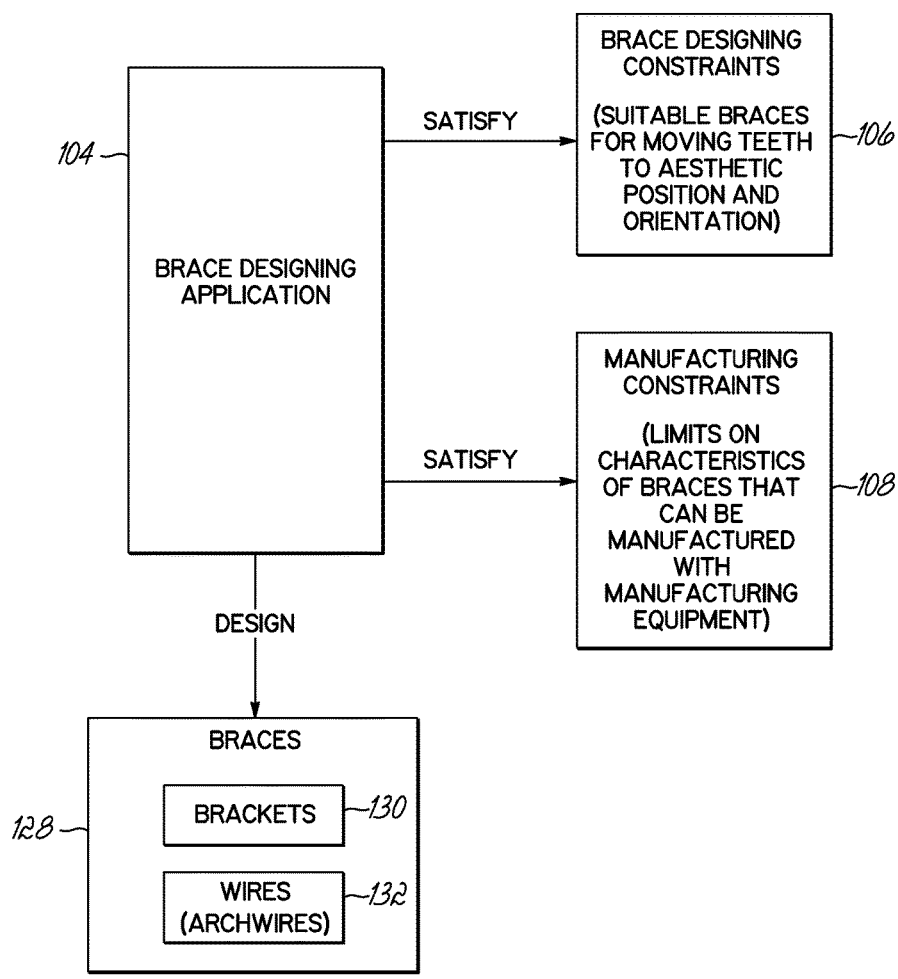
FIG. 4 illustrates a block diagram that shows how a brace designing application is used to design braces while satisfying various design and manufacturing constraints, in accordance with certain embodiments.

FIG. 4 illustrates a block diagram 400 that shows how the brace designing application 104 is used to design braces while satisfying various design and manufacturing constraints, in accordance with certain embodiments.

The brace designing application 104 may design braces 128 that include stock brackets 130 that are to be machined, and wires 132 based on satisfying brace designing constraints 108 and brace manufacturing constraints 106. The brace designing constraints 108 are constraints that are for designing braces suitable for moving teeth to an aesthetic or medically prescribed position and orientation, and the manufacturing constraints 106 are limits on characteristics of braces that can be manufactured or machined by the brace manufacturing machinery 126.

Certain embodiments model bracket placement and archwire smoothing mathematically, as constrained optimization problems. Depending on the type of brackets in use, a combination of various components may be employed to set up the overall optimization problem. A framework is established to provide necessary hierarchies and data flow management. This ensures that the placement optimization for additional brackets with possibly new forms of constraints may be implemented in certain embodiments with relative ease.

Figure 5:
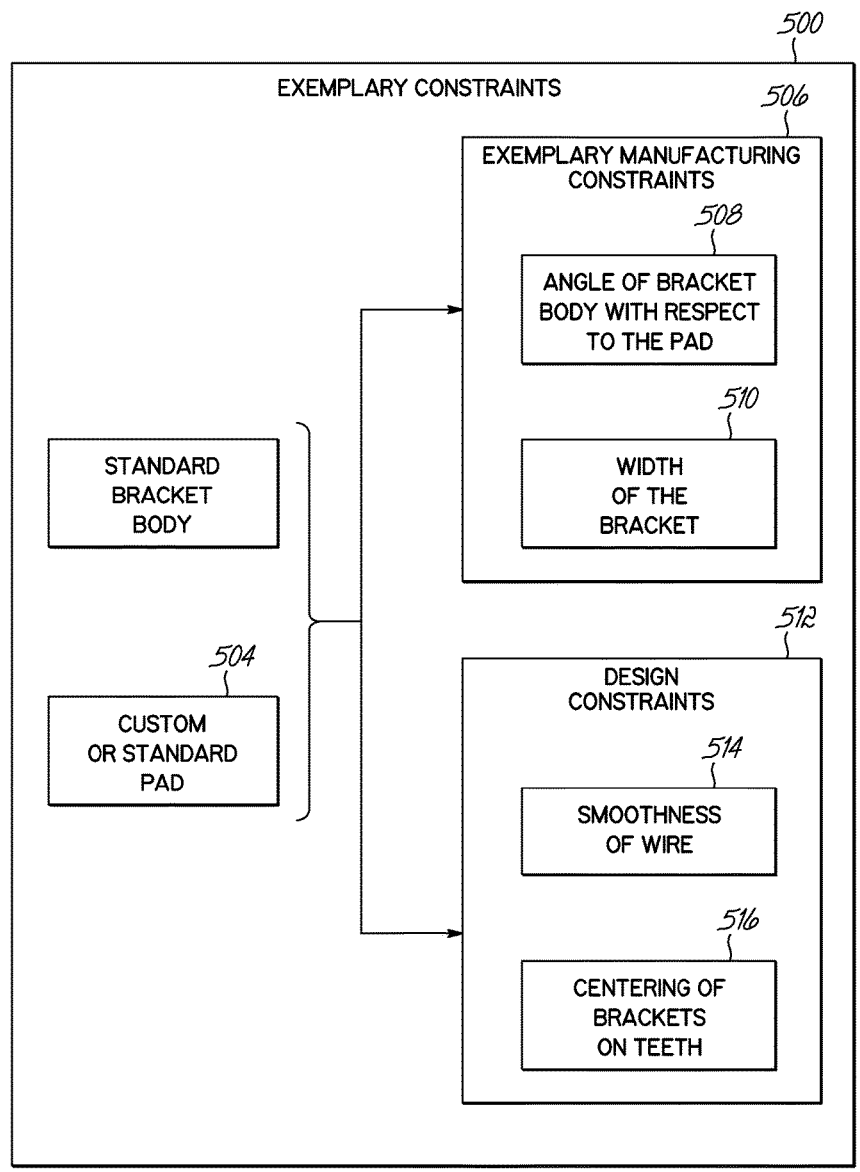
FIG. 5 illustrates a block diagram that show exemplary constraints, in accordance with certain embodiments.

FIG. 5 illustrates a block diagram 500 that shows exemplary constraints, in accordance with certain embodiments. In certain embodiments standard (i.e., stock) bracket body and a custom or standard pad 504 are used. Exemplary manufacturing constraints 506 may include the limitations on the allowed angle of the bracket body with respect to the pad 508 and limitations on the width of the bracket 510. Exemplary design constraints 512 may include the smoothness of the wire 514 and the centering of brackets on teeth 516.

Figure 6:
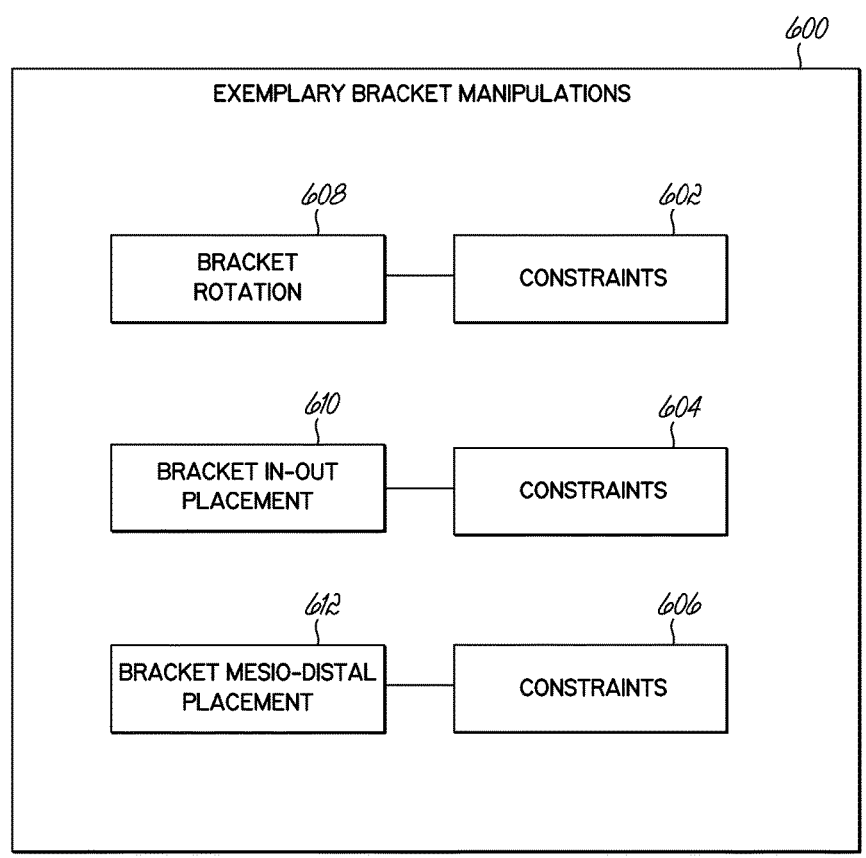
FIG. 6 illustrates a block diagram that shows constraints associated with exemplary bracket manipulations, in accordance with certain embodiments.

FIG. 6 illustrates a block diagram 600 that shows constraints associated with exemplary bracket manipulations, in accordance with certain embodiments. FIG. 6 shows constraints 602, 604, 606 corresponding to bracket rotation 608, bracket in-out placement 610, and bracket mesio-distal placement 612. The constraints 602, 604, 606 are to be satisfied while designing the braces by the brace designing application 104.

In certain embodiments, as shown in FIG. 6, the degrees of freedom of the entire bracket/wire assembly (of one arch) are broken down into applicable components. For example, in the case of Self-ligating (SL) brackets, three degrees of freedom are allowed to be manipulated: bracket rotation (about the occlusal-gingival axis), bracket facio-lingual (in-out) placement, and bracket mesio-distal placement. Each component may be subjected to certain constraints. The goal of the optimization is to achieve multiple objectives simultaneously, including the satisfaction of all constraints, smooth archwires, and generate minimum bracket heights.

Figure 7:
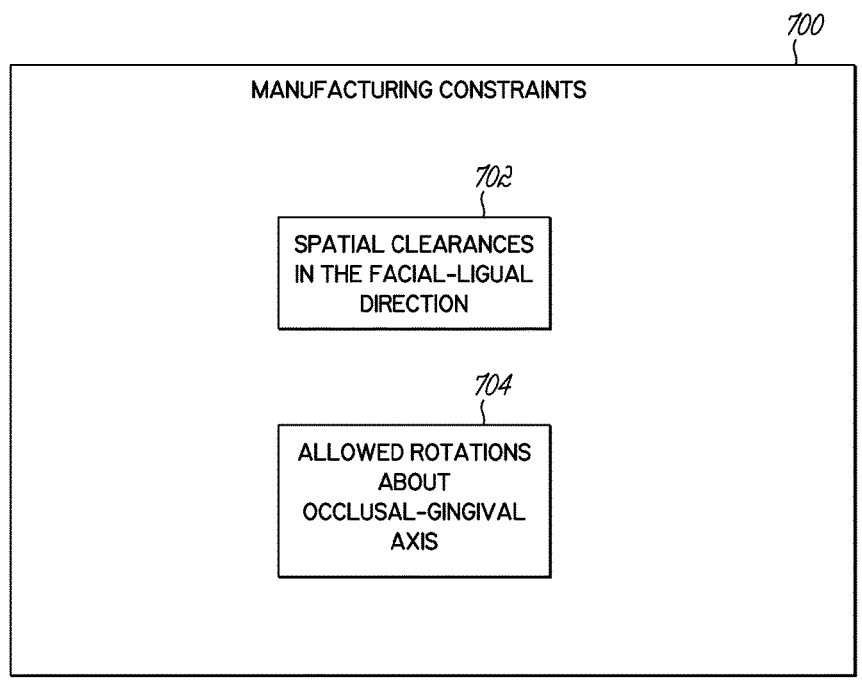
FIG. 7 illustrates block diagram that shows exemplary manufacturing constraints, in accordance with certain embodiments.

FIG. 7 illustrates block diagram 700 that shows exemplary manufacturing constraints, in accordance with certain embodiments. The manufacturing constraints may include spatial clearances in the facial-lingual direction 702 and allowed rotations about the occlusal-gingival axis.

It should be noted, that a majority of the constraints may be related to manufacturability. For instance, as shown in FIG. 7, Self-ligating brackets may require various spatial clearances in the facio-lingual direction to ensure proper access of welding tools; while rhomboid brackets impose limitations on rotations about the occlusal-gingival axis, so that the slot to be subsequently machined can securely house the wire. Such constraints are formulated as translational and rotational constraints, respectively.

Figure 8:
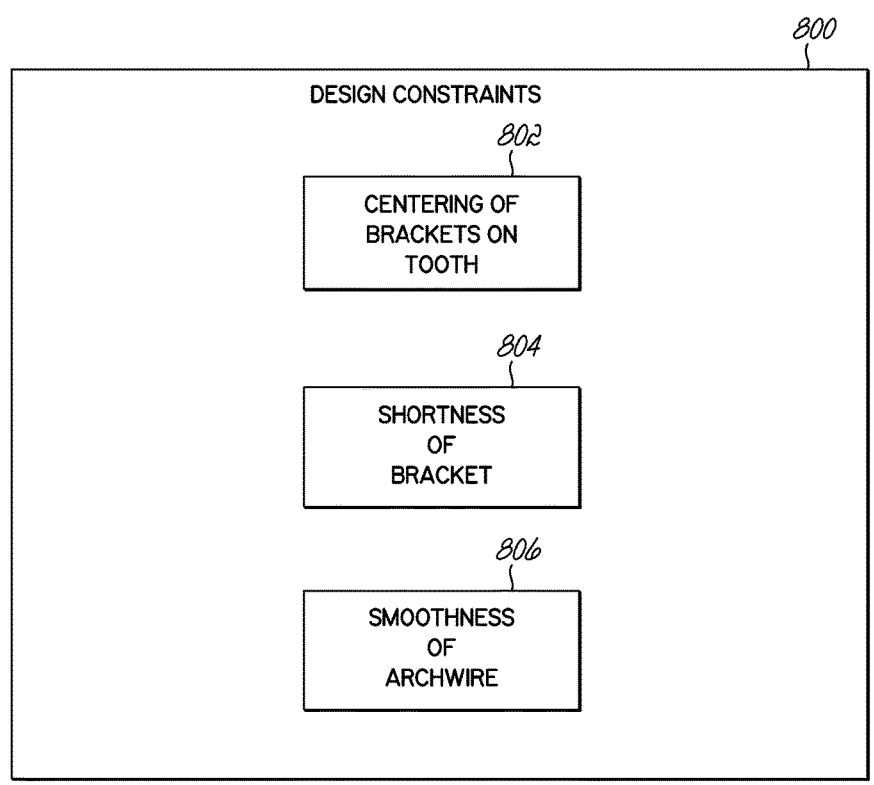
FIG. 8 illustrates a block diagram that shows exemplary design constraints, in accordance with certain embodiments.

FIG. 8 illustrates a block diagram 800 that shows exemplary design constraints, in accordance with certain embodiments. The design constraints may include constraints on the centering of brackets on tooth 802, the shortness of brackets 804, and the smoothness of the archwire 806.

Figure 9:
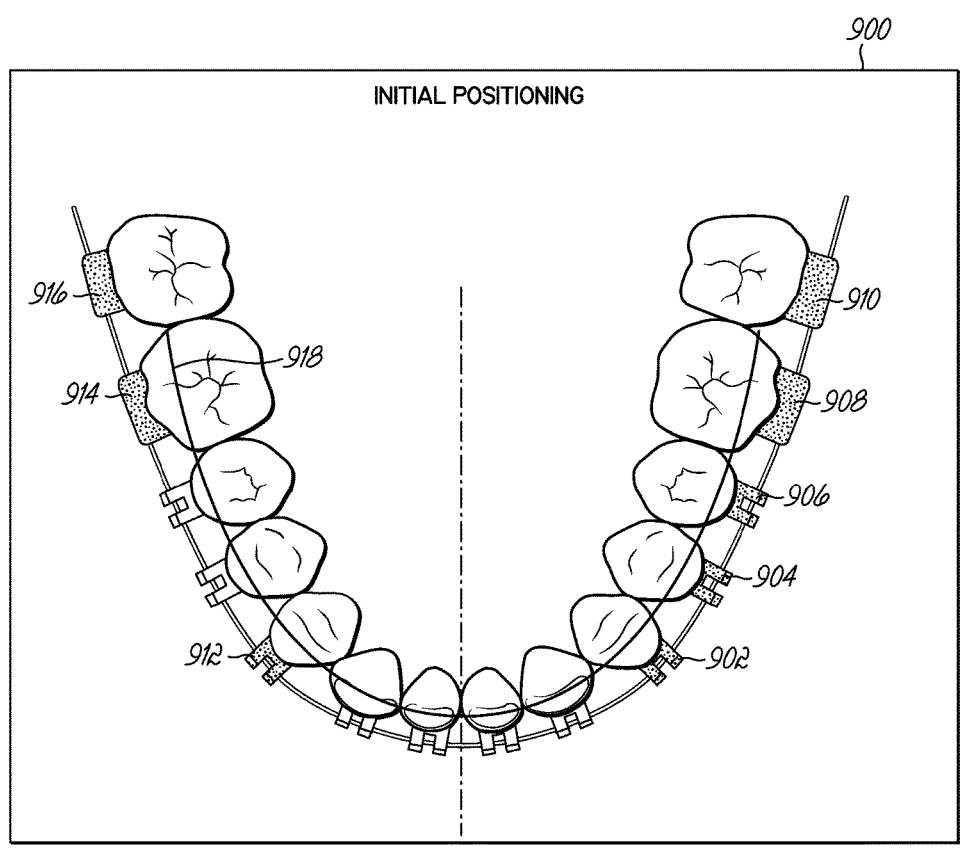
FIG. 9 illustrates a block diagram that shows an initial positioning of brackets and wires on an arch, in accordance with certain embodiments.

FIG. 9 illustrates a block diagram 900 that shows an initial positioning of brackets and wires on an arch, in accordance with certain embodiments. The initial positioning is shown on the display device 116 by the brace designing application 104. In the initial positioning, some of the brackets (e.g., brackets 902, 904, 906, 908, 912, 914, 916) may be such that certain manufacturing constraints are violated. In certain embodiments such brackets in which manufacturing constraints are not satisfied may be color coded or indicated via other identifying mechanisms in the visual display 118. In some brackets (e.g., bracket 910) all constraints are satisfied.

FIG. 9 also shows a parametric curve 918 that is a representation of the dental arch. The curve 918 is used as a visual representations of the curvature of the dental arch.

Figure 10:
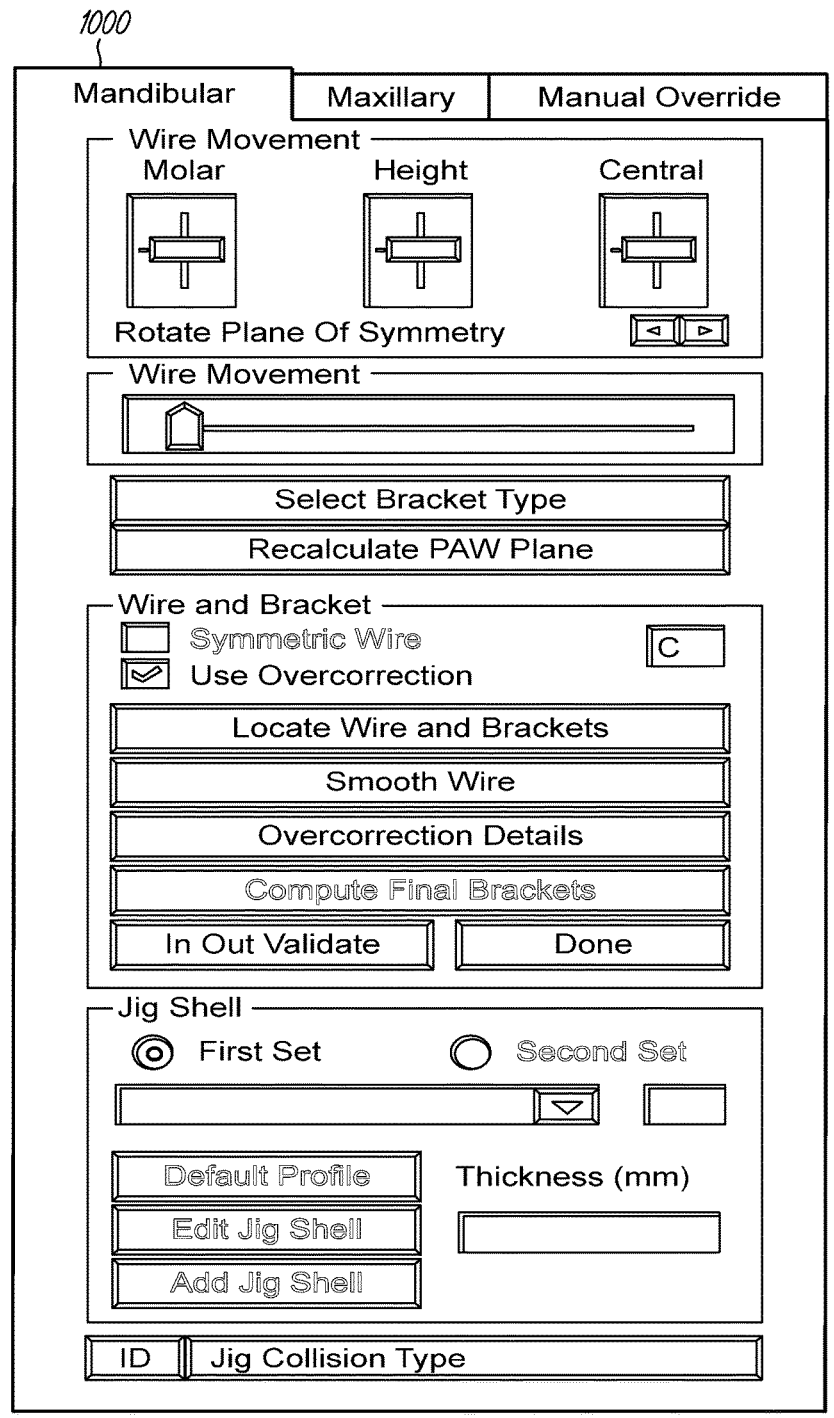
FIG. 10 illustrates a block diagram of a user interface that indicates various parameters that may be adjusted by the brace designing application either automatically or via a technician, in accordance with certain embodiments.

FIG. 10 illustrates a block diagram 1000 of a user interface that indicates various parameters that may be adjusted by the brace designing application 104 either automatically or via a technician, in accordance with certain embodiments. It may be seen that various selections such as the mandibular or maxillary arch, amount of wire movements, controls for locating wires and brackets, etc. are shown in FIG. 10.

Figure 11:
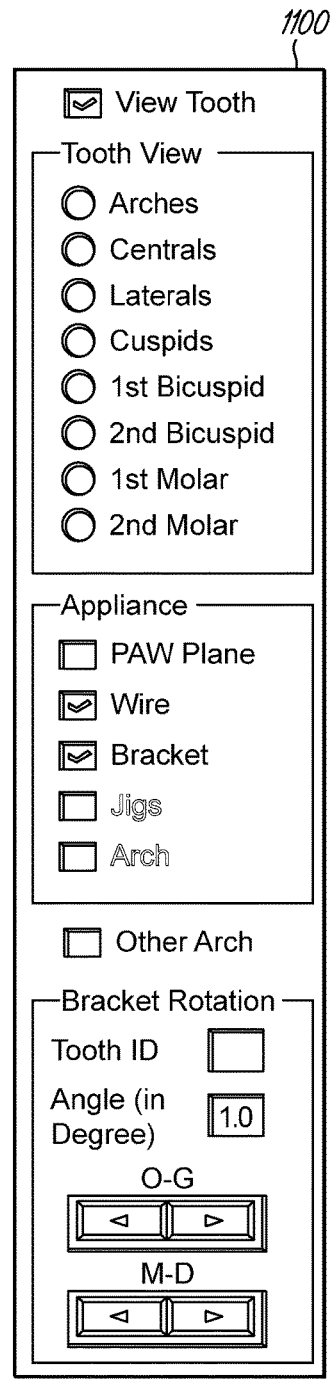
FIG. 11 illustrates a block diagram of another user interface that indicates various parameters that may be adjusted by the brace designing application either automatically or via a technician, in accordance with certain embodiments.

FIG. 11 illustrates a block diagram of another user interface 1100 that indicates various parameters that may be adjusted by the brace designing application 104 either automatically or via a technician, in accordance with certain embodiments. It may be seen that selections for various tooth views and bracket rotations, etc., are shown in FIG. 11.

Figure 12:
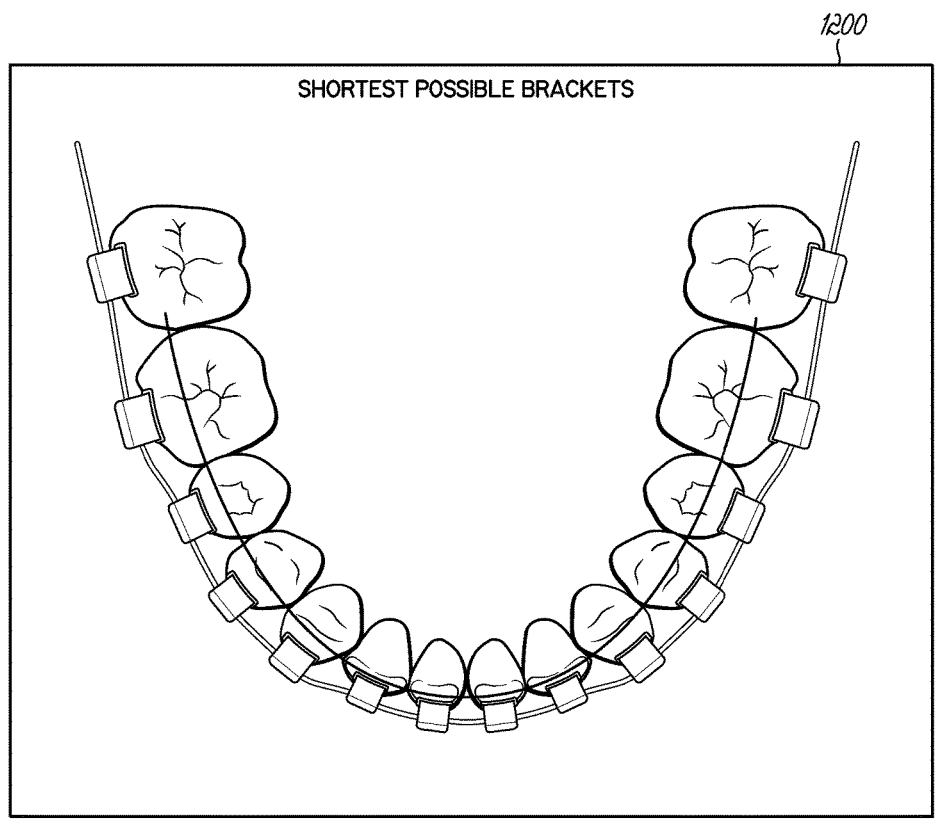
FIG. 12 illustrates a block diagram that shows a first phase in which shortest possible brackets are designed, in accordance with certain embodiments.

FIG. 12 illustrates a block diagram 1200 that shows a first phase in which shortest possible brackets are designed, in accordance with certain embodiments. The brackets are expected to be as "short" as possible, since taller brackets may increase patient discomfort, or interfere with mastication. The constraints for shortest bracket may also be formulated as translational constraints in which certain heuristics may be involved, in order to reach an optimal result in the majority of cases. While designing the shortest possible brackets, the brace designing application 104 ensures that the brace manufacturing constraints 106 and the brace designing constraints 108 are not violated.

Figure 13:
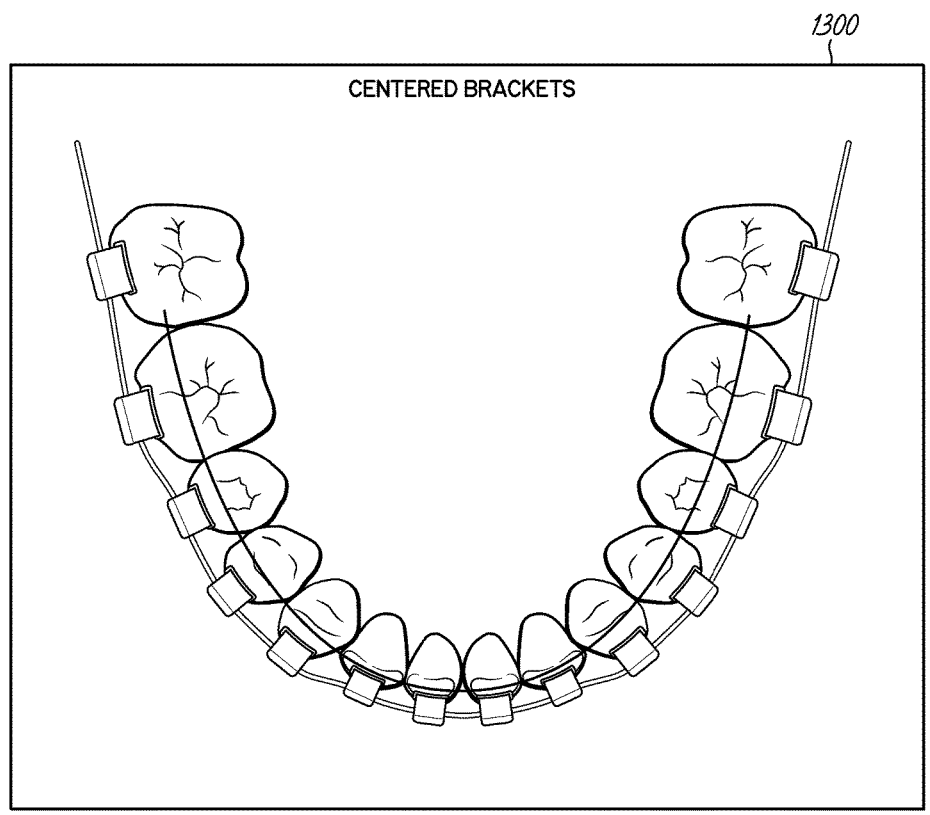
FIG. 13 illustrates a block diagram that shows a second phase in which brackets are centered on teeth, in accordance with certain embodiments.

FIG. 13 illustrates a block diagram 1300 that shows a second phase in which brackets are centered on teeth, in accordance with certain embodiments. The centering of the brackets on teeth is performed subsequent to designing the shortest possible brackets.

The constraints for the centering of brackets are for aesthetic or functional considerations. For instance, it is generally considered visually pleasing that each bracket be centered around the climax point on the face of the tooth. These constraints may also be formulated as translational constraints, and certain heuristics may be involved, in order to reach an optimal result in the majority of cases. For example, one way to limit the range of bracket deviation from the climax point is to introduce an imaginary spring that pulls the bracket back, when it moves away too far.

Figure 14:
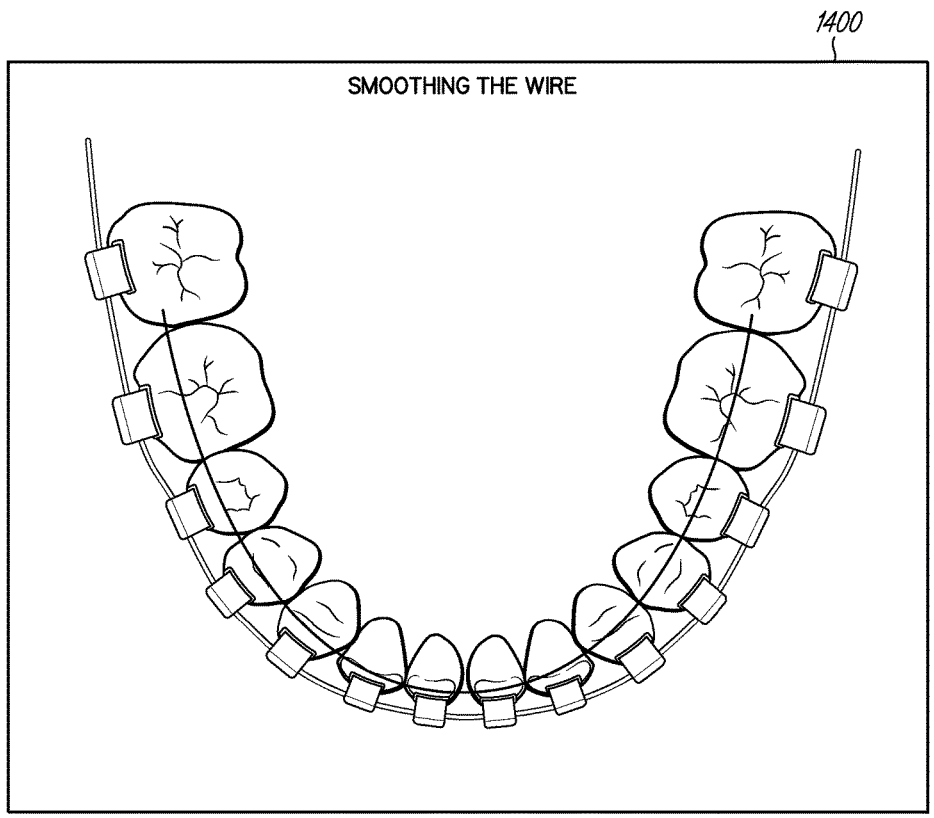
FIG. 14 illustrates a block diagram that shows smoothing of an archwire passing through the slots of brackets, in accordance with certain embodiments.

FIG. 14 illustrates a block diagram 1400 that shows smoothing of an archwire passing through the slots of brackets, in accordance with certain embodiments. The smoothing of the archwire is performed after designing the shortest brackets and centering the brackets on the teeth. However, while smoothing the archwire the brackets may have to be redesigned to some extent and bracket placements may have to be altered, and such modifications are performed iteratively.

The smoothness of the archwire shown in FIG. 14 may be modeled in the perspective of energy inherent in the curve shape. For example, first-order derivatives integrated over the curve may be viewed as an approximation of the "stretching" energy; and second-order derivatives integrated over the curve can be viewed as an approximation of the "bending" energy. Minimizing the sum of such energy terms for the entire archwire, therefore, produces the effect of making it shorter in length (least stretched), and flatter in curviness (least bent), respectively.

Alternatively, certain embodiments focus on inflections in the curve shape (which constitute a major source of visual unpleasantness) and view them as internal stress that are to be relieved. A force field may be constructed over the entire assembly as a result of this stress. Using Newton's second law of motion, adjustments in bracket locations may be computed in response to this force field, in an imaginary time domain. This simulates the manual process of fine-tuning bracket positions while simultaneously visualizing the shape of the archwire.

Yet another embodiment improves the wire smoothness iteratively by a predictor-corrector scheme. For each iteration, a smooth fit curve is computed from the bracket slot locations. This fit curve represents a prediction of the ideal smooth wire. The bracket placement is then adjusted to approach the fit curve, while maintaining satisfaction of constraints. The new bracket slot locations in turns correct, or update, the prediction for the next iteration. In certain embodiments, the method converges in less than five iterations.

Figure 15:
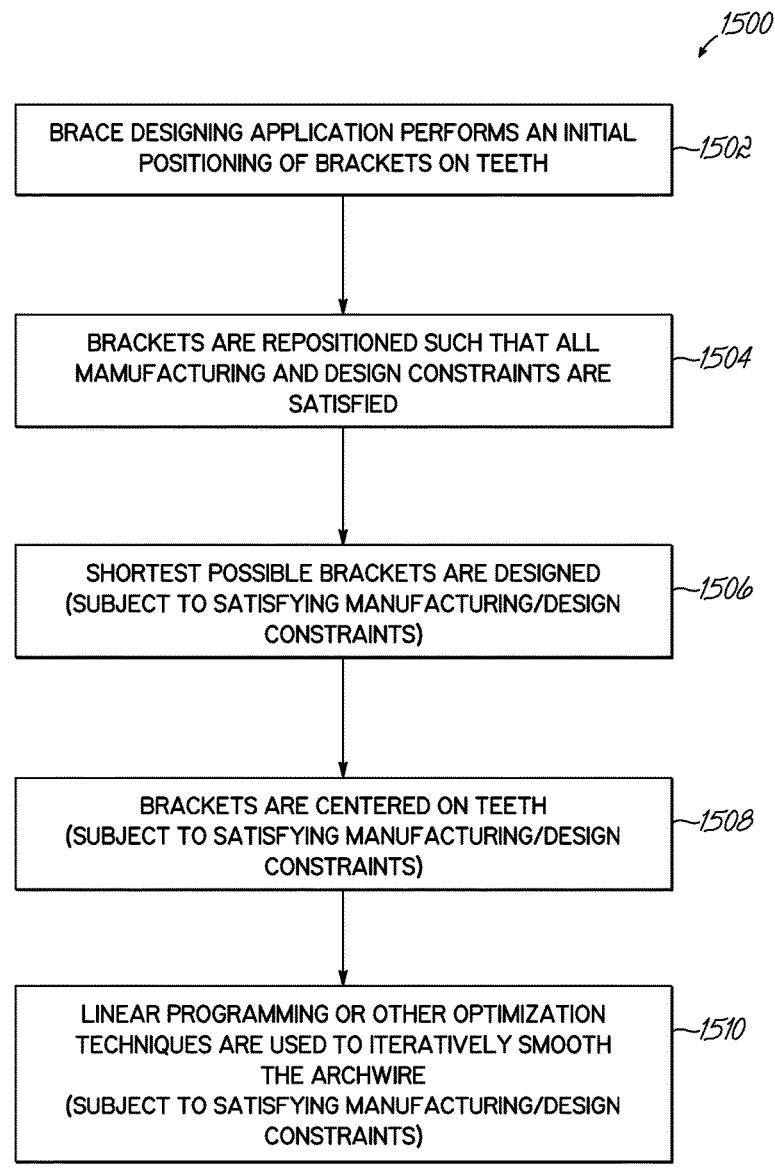
FIG. 15 illustrates a first flowchart that shows the constrained optimization of orthodontic bracket placement and archwire smoothing, in accordance with certain embodiments.

FIG. 15 illustrates a first flowchart 1500 that shows the constrained optimization of orthodontic bracket placement and archwire smoothing, in accordance with certain embodiments. The operations shown in FIG. 15 may be performed by the brace designing application 104 that executes in the computational device 102.

Control starts at block 1502 in which the brace designing application 104 performs an initial positioning of brackets on teeth. Brackets are then repositioned (at block 1504) such that all manufacturing and design constraints are satisfied.

Control proceeds to block 1506, in which shortest possible brackets are designed by the brace designing application 104, while satisfying manufacturing constraints. Subsequently at block 1508, brackets are centered on teeth while the manufacturing and design constraints are also satisfied. Linear programming or other optimization techniques are used (at block 1510) to iteratively smooth the archwire, while the manufacturing and design constraints are also satisfied.

Figure 16:
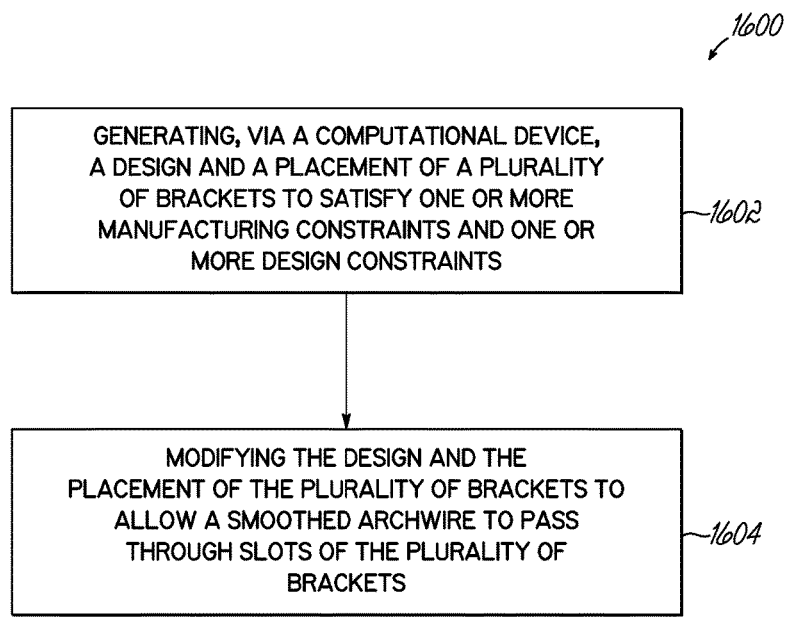
FIG. 16 illustrates a second flowchart that shows the constrained optimization of orthodontic bracket placement and archwire smoothing, in accordance with certain embodiments.

FIG. 16 illustrates a second flowchart 1600 that shows the constrained optimization of orthodontic bracket placement and archwire smoothing, in accordance with certain embodiments. The operations shown in FIG. 16 may be performed by the brace designing application 104 that executes in the computational device 102.

Control starts at block 1602 in which a computational device 102 generates a design and a placement of a plurality of brackets to satisfy one or more manufacturing constraints 106 and one or more design constraints 108. The design and the placement of the plurality of brackets are modified (at block 1604) to allow a smoothed archwire to pass through slots of the plurality of brackets.

Figure 17:
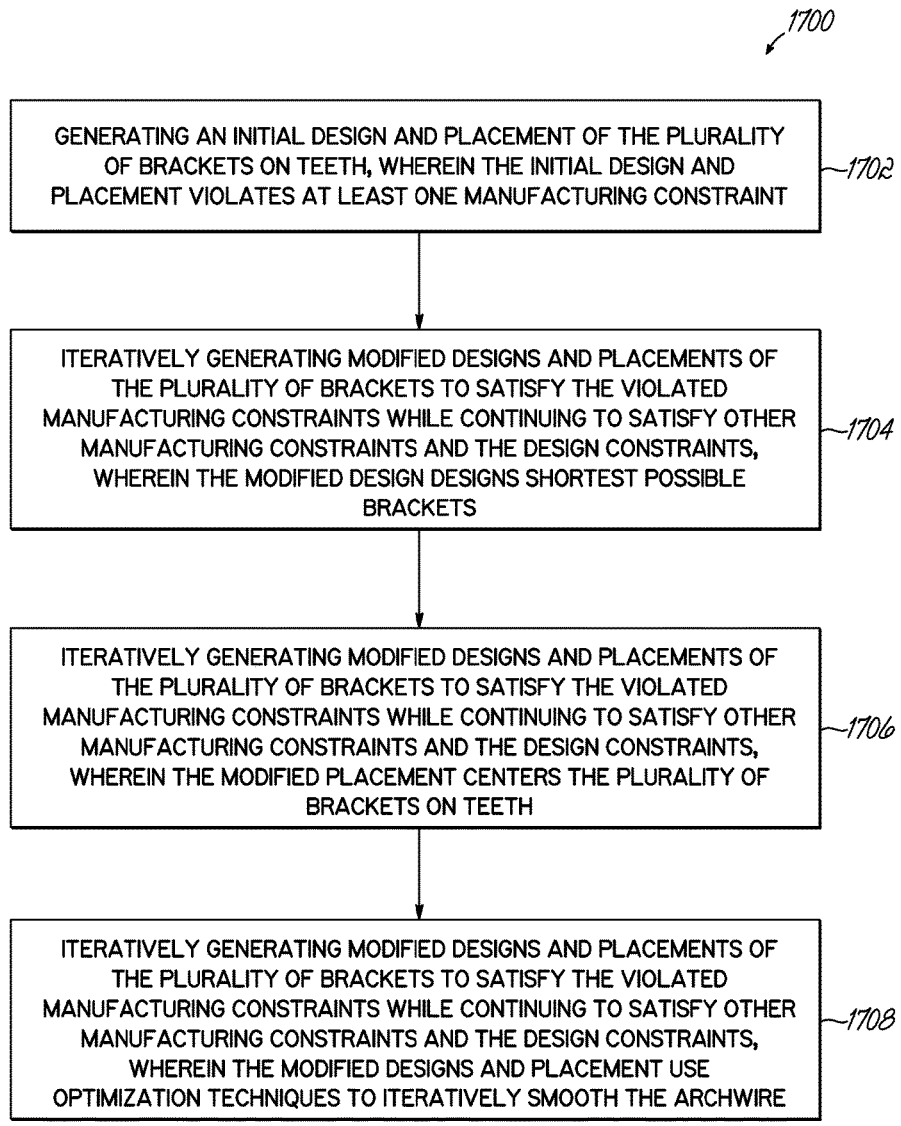
FIG. 17 illustrates a third flowchart that shows the constrained optimization of orthodontic bracket placement and archwire smoothing, in accordance with certain embodiments.

FIG. 17 illustrates a third flowchart 1700 that shows the constrained optimization of orthodontic bracket placement and archwire smoothing, in accordance with certain embodiments. The operations shown in FIG. 17 may be performed by the brace designing application 104 that executes in the computational device 102.

Control starts at block 1702 in which a brace designing application 104 generates an initial design and placement of the plurality of brackets on teeth, wherein the initial design and placement violates at least one manufacturing constraint.

Control proceeds to block 1704, where the brace designing application 104 iteratively generates modified designs and placements of the plurality of brackets to satisfy the violated manufacturing constraint while continuing to satisfy other manufacturing constraints and the design constraints, where the modified design designs shortest possible brackets.

Control then proceeds to block 1706, where the brace designing application 104 iteratively generates modified designs and placements of the plurality of brackets to satisfy the violated manufacturing constraint while continuing to satisfy other manufacturing constraints and the design constraints, where the modified placements center the plurality of brackets on teeth. Control then proceeds to block 1708, where the brace designing application 104 iteratively generates modified designs and placements of the plurality of brackets to satisfy the violated manufacturing constraint while continuing to satisfy other manufacturing constraints and the design constraints, where the modified designs and placements use optimization techniques to iteratively smooth the archwire.

Therefore, FIG. 1-17 illustrate certain embodiments in which a brace designing application iteratively designs a brace to satisfy manufacturing constraints and design constraints, while at the same time smoothing the archwire.

Additional Details of Embodiments

Certain operations described in the figures may be implemented as a method, apparatus or computer program product using techniques to produce software, firmware, hardware, or any combination thereof. Additionally, certain embodiments may take the form of a computer program product embodied in one or more computer readable storage medium(s) having computer readable program code embodied therein.

A computer readable storage medium may include an electronic, magnetic, optical, electromagnetic, or semiconductor system, apparatus, or device, or any suitable combination of the foregoing. The computer readable storage medium may also comprise an electrical connection having one or more wires, a portable computer diskette or disk, a hard disk, a random access memory (RAM), a read-only memory (ROM), an erasable programmable read-only memory (EPROM or Flash memory), a portable compact disc read-only memory (CD-ROM), an optical storage device, a magnetic storage device, etc. A computer readable storage medium may be any tangible medium that can contain, or store a program for use by or in connection with an instruction execution system, apparatus, or device.

A computer readable signal medium includes a propagated data signal with computer readable program code embodied therein. A computer readable signal medium may be any computer readable medium that is not a computer readable storage medium and that can communicate, propagate, or transport a program for use by or in connection with an instruction execution system, apparatus, or device. The computer readable storage medium is different from the computer readable signal medium.

Computer program code for carrying out operations for aspects of the present invention may be written in any combination of one or more programming languages.

Aspects of the present invention are described below with reference to flowchart illustrations and/or block diagrams of methods, system and computer program products according to certain embodiments. At least certain operations that may have been illustrated in the figures show certain events occurring in a certain order. In alternative embodiments, certain operations may be performed in a different order, modified or removed. Additionally, operations may be added to the above described logic and still conform to the described embodiments. Further, operations described herein may occur sequentially or certain operations may be processed in parallel. Yet further, operations may be performed by a single processing unit or by distributed processing units. Computer program instructions can implement the blocks of the flowchart. These computer program instructions may be provided to a processor of a computer for execution.

Figure 18:
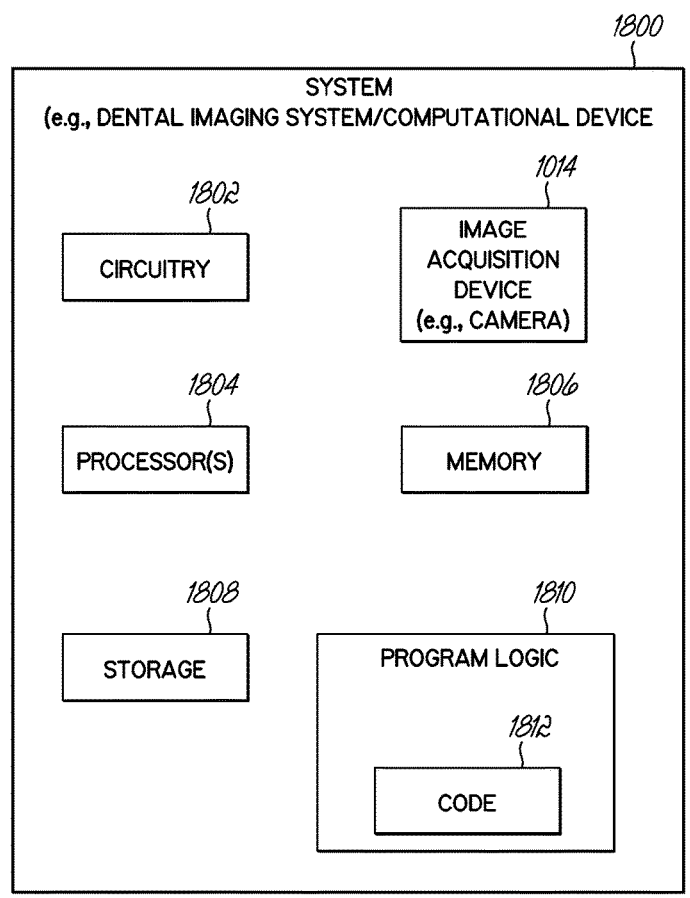
FIG. 18 illustrates a block diagram of a system in which the brace designing application may execute, in accordance with certain embodiments.

FIG. 18 illustrates a block diagram of a computer system 1800 (e.g., the computational device 102 shown in FIG. 1) used to design braces, in accordance with certain embodiments. In certain 1800 may include a circuitry 1802 that may in certain embodiments include at least a processor 1804. The processor 1804 may comprise any suitable processor known in the art, such as, an arithmetic logical unit, a central processing unit, a circuitry that perform operations, hardware that performs instructions of a computer program, a microprocessor, a parallel processor, an array processor, a vector processor, a transistorized central processing unit, a microcontroller, a logic circuitry, etc. Any device that manipulates digital information based on one or more operational instructions or in a predefined manner is an example of the processor 1804. The system 1800 may also include a memory 1806 (e.g., a volatile memory device), and storage 1808. The storage 1808 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 1808 may comprise an internal storage device, an attached storage device and/or a network accessible storage device. The system 1800 may include a program logic 1810 including code 1812 that may be loaded into the memory 1806 and executed by the processor 1804 or circuitry 1802. In certain embodiments, the program logic 1810 including code 1812 may be stored in the storage 1808. In certain other embodiments, the program logic 1810 may be implemented in the circuitry 1802. Therefore, while FIG. 18 shows the program logic 1810 separately from the other elements, the program logic 1810 may be implemented in the memory 1806 and/or the circuitry 1802. In certain embodiments, the system 1800 may include an image acquisition device 1014, such as a camera.

Figure 19A:
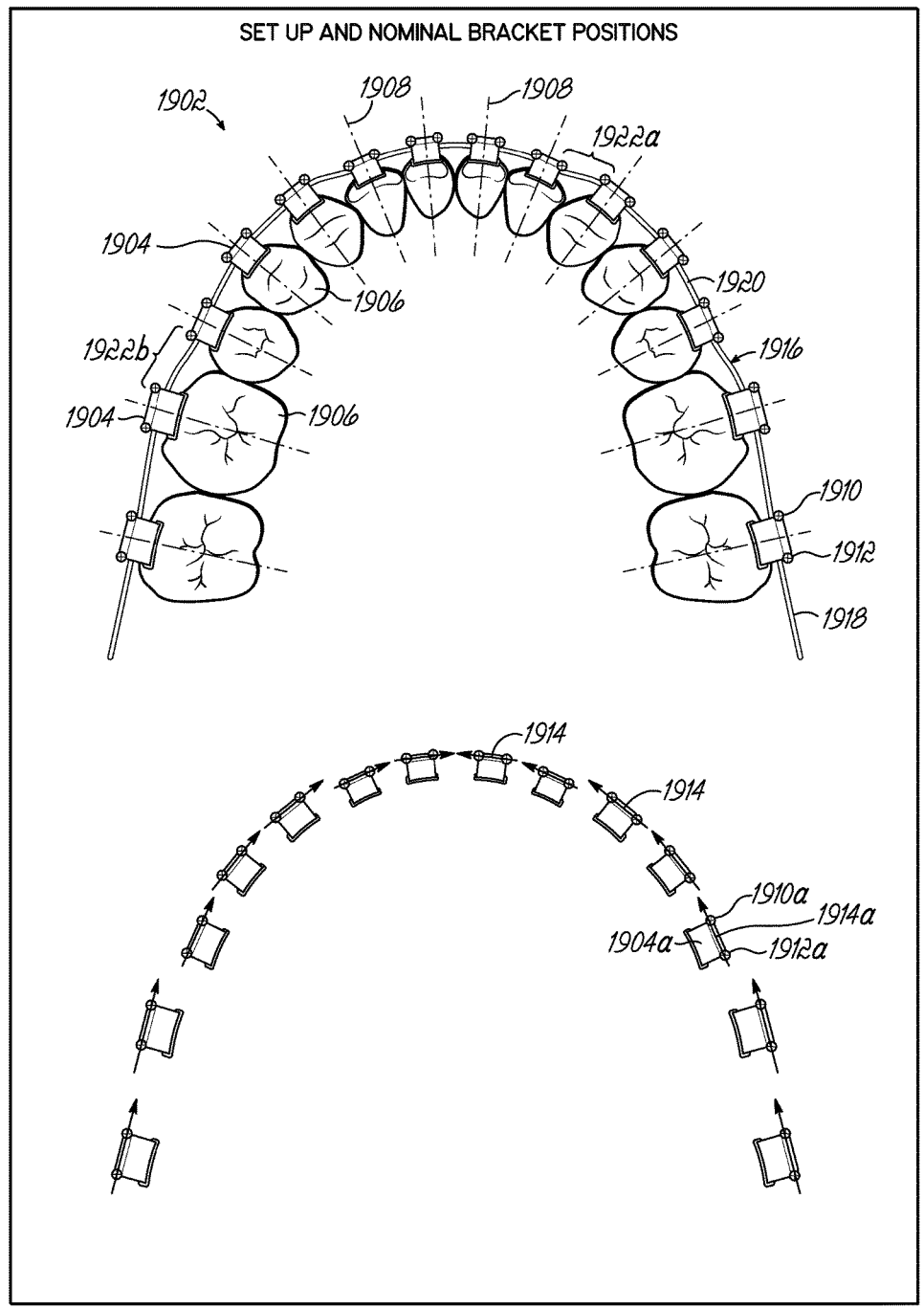
FIG. 19A illustrates a block diagram that shows a nominal bracket positioning of virtual brackets and an archwire disposed thereon, as well as a similar set of brackets with a matching vector applied thereto, in accordance with certain embodiments.

FIG. 19A illustrates a nominal bracket position 1902, also referred to herein as a nominal bracket layout 1902. The nominal bracket layout 1902 refers to the position of a set of virtual brackets 1904 on a digital representation of a set of teeth 1906. Each tooth 1906 includes a corresponding bracket 1904 positioned thereon in accordance with the specifications of the nominal bracket layout 1902. The nominal bracket layout may be customized by a user or company by setting variables associated with an underlying positioning algorithm or routine. As shown in FIG. 19A, one example of a nominal bracket layout 1902 may be to position a virtual bracket 1904 on the corresponding digital representation of a tooth 1906 in the direct center of the tooth, at a neutral rotation, and at a set distance away from the tooth. In an embodiment of the invention, the nominal bracket layout 1902 may position each virtual bracket 1904 along the facial axis of the clinical crown (FACC) to "center" the bracket 1904 on the tooth 1906. A reference line 1908 for each tooth 1906 is provided along the FACC in FIG. 19A and each corresponding tooth 1906 is aligned thereby.

As shown in FIG. 19A, each virtual bracket 1904 includes a first end 1910 and a second end 1912 along the top of the bracket 1904. By connecting the first end 1910 and the second end 1912 for each virtual bracket 1904, a vector 1914 may be derived. The vector 1914 for each virtual bracket 1904 and tooth 1906 is oriented parallel to the top of the bracket 1904. Thus, by using vectors 1914, one can determine a best fit curve or path 1916 for a virtual archwire 1918 connected with each bracket 1904. The path 1916 generally follows along in parallel with each respective vector 1914 with a set of connecting segments 1920 interspersed with the vectors 1914 to make path 1916 continuous. For example, as shown in FIG. 19A, the vector 1914A is derived from the placement of the first end 1910A and the second end 1912A of the virtual bracket 1904A. When vector 1914A of virtual bracket 1904A is combined with the other vectors 1914 generated from each bracket 1904, the path 1916 of the corresponding virtual archwire 1918 is constructed and attained. Once path 1916 is constructed, one or more areas of inflection 1922 such as area 1922A and area 1922B may be realized and attended to.

In general, orthodontic efficiencies are best realized through a smooth archwire with minimized areas of inflection 1922. As such, based on the path 1916 of the virtual archwire 1918, a particular virtual bracket 1904 may be selected for re-positioning in an effort to minimize a particular area of inflection 1922. The re-positioning may take the form of adjusting the height of the virtual bracket 1904, adjusting the rotation of the virtual bracket 1904, adjusting the mesio-distal placement of the virtual bracket 1904, or a combination thereof.

Figure 19B:
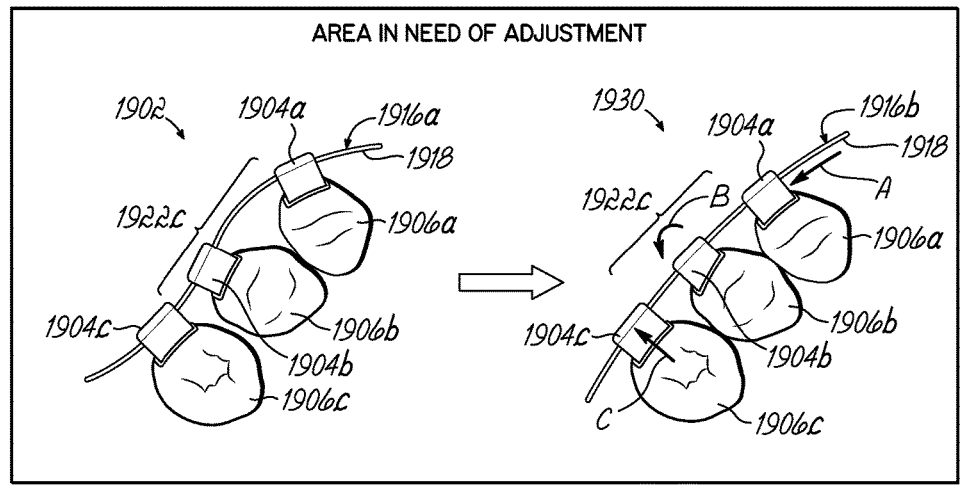
FIG. 19B illustrates a block diagram that shows a series of three teeth with corresponding virtual brackets positioned thereon along with an archwire in need of adjustment, in accordance with certain embodiments.

An exemplary area of inflection 1922C is shown in FIG. 19B, whereby the normal bracket layout 1902 is transformed into an updated bracket layout 1930 by re-positioning virtual bracket 1904A, virtual bracket 1904B, and virtual bracket 1904C in the area of inflection 1922C. The re-positioning of the associated brackets 1904 smooths path 1916A into path 1916B through the re-positioning. Specifically, virtual bracket 1904A is adjusted mesial-distally in the direction of arrow A on tooth 1906A; virtual bracket 1904B is rotated by changing the back surface 1932 in the direction of arrow B; and the height of virtual bracket 1904C is adjusted in the direction of arrow C. These three exemplary adjustments of the virtual brackets 1904 transform path 1916A, associated with the nominal bracket layout 1902, into path 1916B, associated with the updated bracket layout 1930.

Figure 19C:
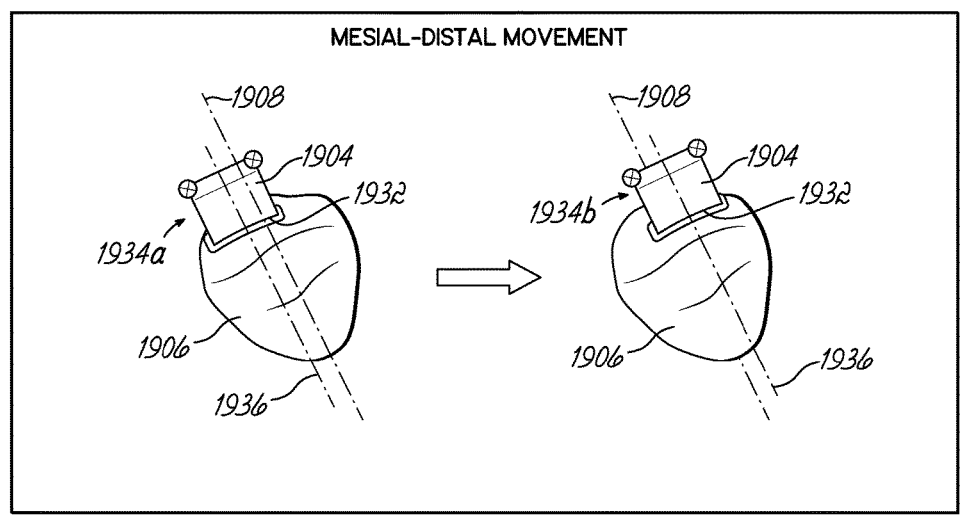
FIG. 19C illustrates a block diagram that shows a tooth and corresponding virtual bracket, whereby the virtual bracket is moved in the mesial-distal direction, in accordance with certain embodiments.

FIG. 19C illustrates mesial-distal movement of the virtual brackets 1904. As described above, each virtual bracket 1904 is positioned on a corresponding tooth 1906 in a position 1934. Before the re-positioning, virtual bracket 1904 is in position 1934A and for reference, includes a midline 1936 to the left of the FACC reference line 1908 of tooth 1906. Once bracket 1904 is re-positioned to position 1934B, the midline 1936 of virtual bracket 1904 is to the right of the FACC reference line 1908 of tooth 1906. The mesial-distal movement shifts the virtual bracket 1904 in a "left" and "right" orientation along the face of the tooth 1906 as required to smooth path 1916.

Figure 19D:
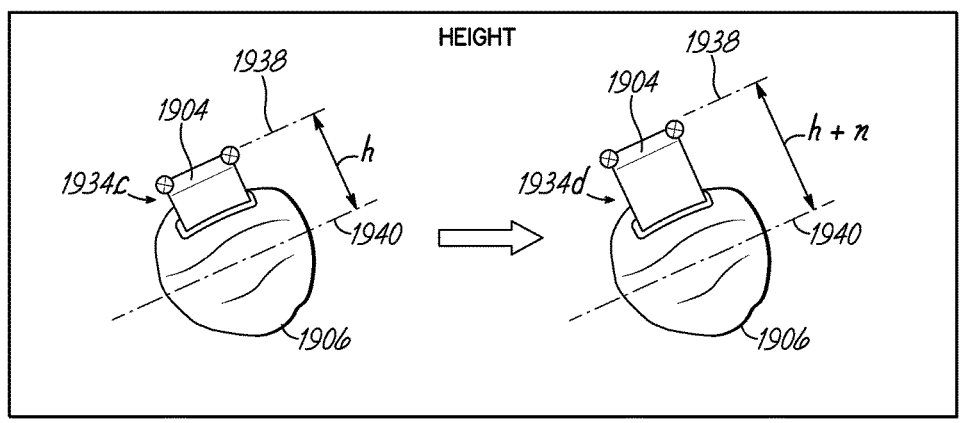
FIG. 19D illustrates a block diagram that shows a tooth and a corresponding virtual bracket, whereby the height of the virtual bracket is adjusted, in accordance with certain embodiments.

FIG. 19D illustrates height related movement of the virtual brackets 1904. The height movement shifts the virtual bracket 1904 "in" and "out" with respect to the face of the tooth 1906 and may be adjusted to smooth path 1916. Initially, the virtual bracket 1904 of FIG. 19D is oriented in a position 1934C. In position 1934C, a front surface 1936 of the virtual bracket 1904 is spaced a distance "h" away from a general cross-sectional midline 1940 of tooth 1906. To re-position the virtual bracket 1904 to position 1934D, the height of the virtual bracket 1904 is increased such that the front surface 1936 of virtual bracket 1904 is spaced a distance of "h+n" away from midline 1940. An adjusted height of the virtual bracket 1904 may provide a smoother path 1916.

Figure 19E:
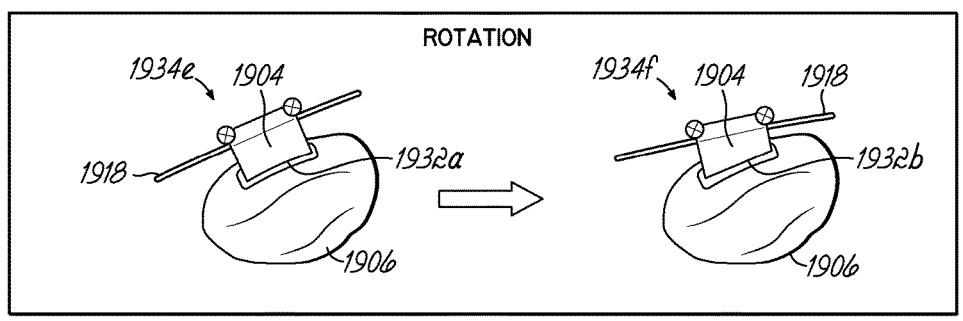
FIG. 19E illustrates a block diagram that shows a tooth and a corresponding virtual bracket having a back surface, whereby the rotation of the slot of the virtual bracket is adjusted by changing the back surface, in accordance with certain embodiments.
Figure 19F:
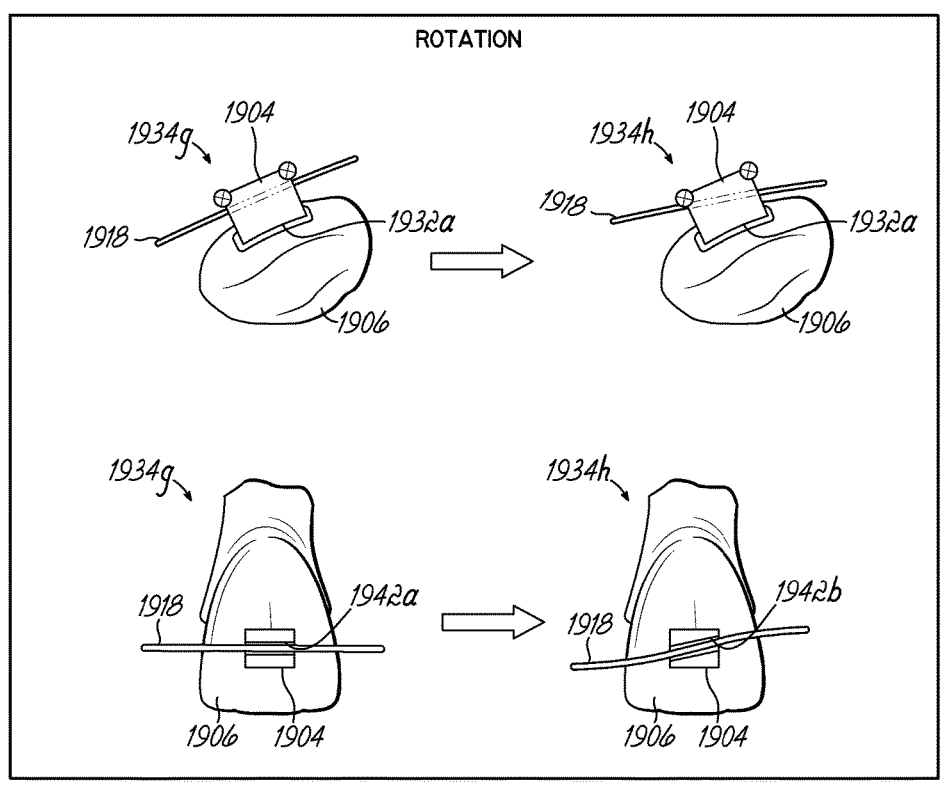
FIG. 19F illustrates a block diagram that shows a tooth and a corresponding virtual bracket, whereby the rotation of the slot of the virtual bracket is adjusted by changing the angle of the slot, in accordance with certain embodiments.

FIGS. 19E and 19F illustrate two different mechanisms for adjusting the rotation of a virtual bracket 1904. In some styles of orthodontic brackets, the back surface 1932 of a virtual bracket 1904 may be adjusted and angled to provide a rotation of the bracket. As shown in FIG. 19E, back surface 1932A is adjusted to back surface 1932B to re-position the virtual bracket 1904 from position 1934E to position 1934F. By adjusting the back surface 1932, the associated virtual bracket 1904 rotates to change the orientation of the virtual archwire 1918 disposed therein. Alternatively, as shown in FIG. 19F, a slot or channel 1942 defined by the virtual bracket 1904 may be adjusted to change the orientation of the virtual archwire 1918 disposed therein. Channel 1942A of virtual bracket 1904 in position 1934G is generally horizontal to allow the virtual archwire 1918 to pass therethrough and conform to the general horizontal channel 1942A. Channel 1942B of virtual bracket 1904 in position 1934H is angled to allow the virtual archwire 1918 to pass therethrough and conform to the angled path of channel 1942B.

In view of the above, at any step in the bracket optimizing process, an orthodontist may use path 1916 and areas of inflection 1922 as a diagnostic tool to visually determine if an orthodontic prescription is appropriate to provide the desired placement of a patient's teeth. After reviewing the path 1916 associated with the virtual archwire 1918, the orthodontist may move or change the prescribed final placement of the teeth to improve the desired placement based upon visual feedback from the digital representation of the set of teeth 1906 with respect to the path 1916 and archwire 1918. For example, if an orthodontist observes a particular area of inflection 1922 that was not foreseen or intended in the initial orthodontic prescription, the orthodontist can move a tooth 1906 as appropriate to correct this issue. As such, the virtual brackets 1904 positioned along the teeth 1906 may be used as a diagnostic tool for orthodontists.

Figure 19G:
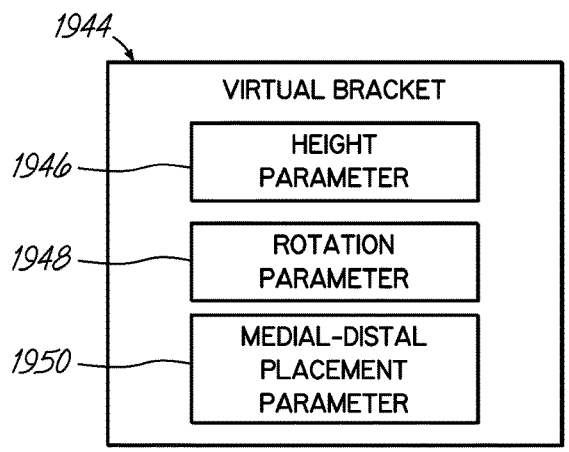
FIG. 19G illustrates a block diagram of a data structure of a virtual bracket, in accordance with certain embodiments.

As shown in FIG. 19G, in an embodiment of the invention, each virtual bracket 1904 may be encapsulated or associated with a virtual bracket data structure 1944. Each virtual bracket data structure 1944 includes a height parameter 1946, a rotation parameter 1948, and a mesio-distal placement parameter 1950. The values of each parameter may be set and updated as necessary to adjust the placement of the associated virtual bracket 1904 on the digital representation of the teeth 1906. For example, the value of height parameter 1946 is adjusted to re-position the associated virtual bracket 1904 in the manner illustrated in FIG. 19D. Likewise, the value of rotation parameter 1948 is adjusted to re-position the associated virtual bracket 1904 in the manner illustrated in FIG. 19E. The value of mesio-distal placement parameter 1950 is adjusted to re-position the associated virtual bracket 1904 in the manner illustrated in either FIG. 19F or FIG. 19G, depending on the underlying type of bracket being modeled.

Figure 19H:
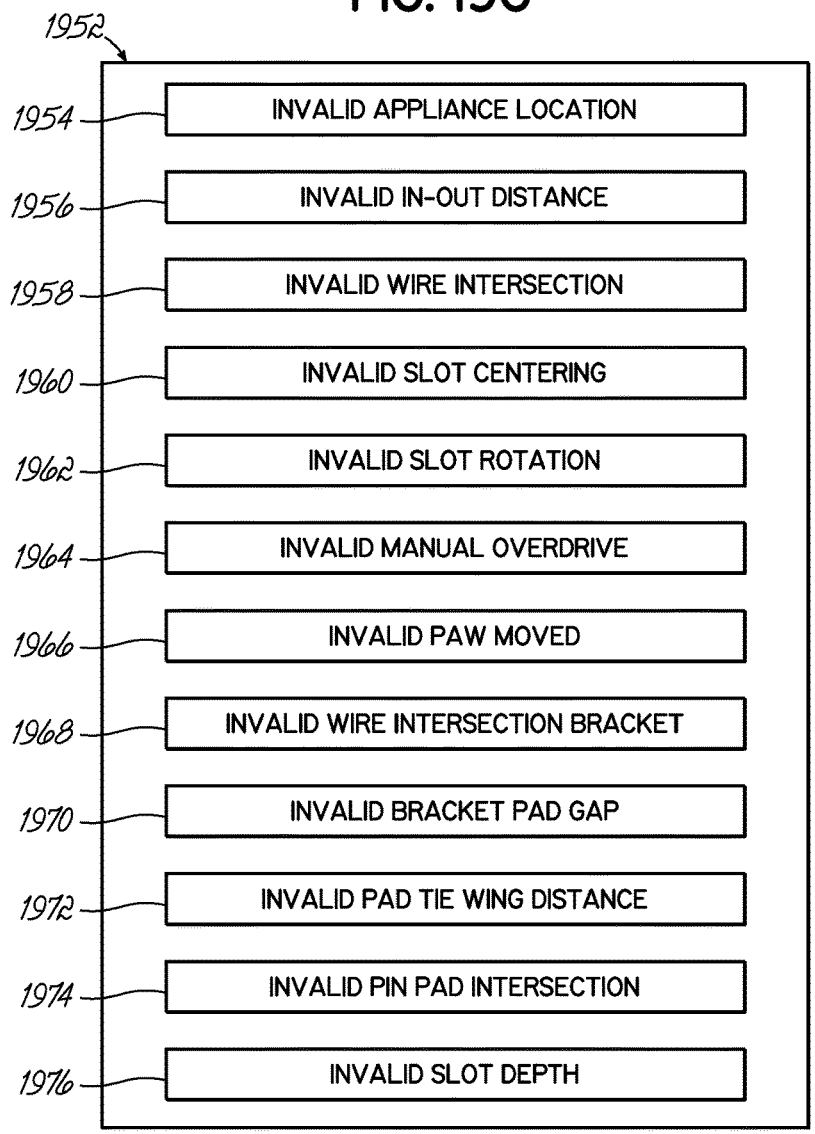
FIG. 19H illustrates a block diagram of a set of constraints, in accordance with certain embodiments.

As shown in FIG. 19H, in an embodiment of the invention, the manufacturing constraints 106 and the design constraints 108 may be merged into a set of constraints 1952. The set of constraints 1952 may include constraints such as an invalid appliance location constraint 1954, an invalid in-out distance constraint 1956, an invalid wire intersection constraint 1958, an invalid slot centering constraint 1960, an invalid slot rotation constraint 1962, an invalid manual override constraint 1964, an invalid PAW moved constraint 1966, an invalid wire intersection bracket constraint 1968, an invalid bracket pad gap constraint 1970, an invalid pad tie wing distance constraint 1972, an invalid pin pad intersection constraint 1974, and an invalid slot depth constraint 1976.

The invalid appliance location constraint 1954 generally relates to the overall location of the virtual bracket 1904 with respect to the underlying tooth 1906. In one embodiment of the invalid appliance location constraint 1954, the constraint includes the maximum allowed deviation of the position 1934 of virtual bracket 1904 from the FA point of the FACC line. In this example, if the position 1934 of the associated bracket 1904 is too far from the FA point of the underlying tooth 1906, the position 1934 is in violation of the invalid appliance location constraint 1954.

The invalid in-out distance constraint 1956 generally relates to the distance between the virtual bracket 1904 and the underlying tooth 1906. In one embodiment of the invalid in-out distance constraint 1956, the constraint includes a range, whereby the virtual bracket 1904 must be positioned within the given range to not violate the constraint. In this embodiment, the distance between the inner face 230 (FIG. 2) of the slot 226 and the rear surface 236 (FIG. 2) of the pad 224 is determined. This distance is then compared to the range specified by the invalid in-out distance constraint 1956 to determine whether the constraint is violated.

The invalid wire intersection constraint 1958 generally relates to the archwire placement inside the bracket slot or channel. Inasmuch as the archwire needs to pass through the side walls of the bracket block without abutting any other faces of the bracket, in one embodiment of the invalid wire intersection constraint 1958, the constraint includes an angle range or a set of appropriate vectors for the archwire within the bracket slot. Thereafter, the actual modeled angle or vector of the archwire within the bracket slot is compared to the invalid wire intersection constraint 1958 to determine whether the constraint is violated.

The invalid slot centering constraint 1960 generally relates to the thickness of the virtual bracket areas around the proposed slot or channel orientation to ensure there is sufficient supporting structure throughout the bracket. In an embodiment of the invalid slot centering constraint 1960, a minimum thickness parameter is provided and each area of the bracket is evaluated to determine whether the bracket thickness meets the minimum thickness parameter. If any area does not meet the minimum thickness parameter, the constraint is violated.

The invalid slot rotation constraint 1962 generally relates to the orientation or depth of the entire length of the slot along the bracket. In an embodiment of the invalid slot rotation constraint 1962, the distance between the most labial slot point and the bracket top surface must be within a particular tolerance. In another embodiment, the smaller of the two in-out distances at the sides of the bracket must be less than a given threshold value.

The invalid manual override constraint 1964 generally relates to the intersection of the archwire plane with a particular tooth. In an embodiment of the invalid manual override constraint 1964, the constraint is violated when a tooth position is manually moved out too far from the plane of the archwire by a technician or orthodontist. The invalid manual override constraint 1964 may also be embodied as an error code or interrupt that prevents the problematic manual movement of a virtual bracket or tooth.

The invalid PAW moved constraint 1966 generally relates to the intersection of the archwire plane generally relates to the intersection of the archwire plane with the set of teeth. In an embodiment of the invalid PAW moved constraint 1966, the constraint is violated when the plane of the archwire is manually moved out too far from one or more teeth by a technician or orthodontist. The invalid PAW moved constraint 1964 may also be embodied as an error code or interrupt that prevents the problematic manual movement of an archwire.

The invalid wire intersection bracket constraint 1968 generally relates to the distance between the front surface 234 (FIG. 2) of the pad 224 and the archwire to ensure there is a minimum distance or gap between the archwire within the slot and the front surface 234 of the pad 224. In an embodiment of the invalid wire intersection bracket constraint 1968, a threshold is provided and the constraint is violated if the distance between the inner face 230 (FIG. 2) of the slot 226 and the front surface 234 of the pad 224 is less than the given threshold.

The invalid bracket pad gap constraint 1970 generally relates to the tilt of the virtual bracket body with respect to the pad 224 (FIG. 2). In an embodiment of the invalid bracket pad gap constraint 1970, the constraint is violated if a gap is detected between the body of the virtual bracket and the pad due to excessive tilt of the bracket body with respect to the pad. A gap threshold may be specified, whereby the constraint is violated if the gap is beyond the size threshold. Alternatively, the constraint may be violated if any gap is detected.

The invalid pad tie wing distance constraint 1972 generally relates to the spacing of the tie wing of the virtual bracket relative to the pad. In an embodiment of the invalid pad tie wing distance constraint 1972, a minimum threshold is provided, whereby the constraint is violated if the distance between the tie wing 221 (FIG. 2) is spaced less than the minimum threshold from the front surface 234 of the pad 224. This insures there is a minimum distance between the tie wing and the pad surface.

The invalid pin pad intersection constraint 1974 generally relates to the depth of a locking pin disposed in the virtual bracket. In some style of brackets, a locking pin is passed generally horizontally through a portion of the bracket to lock the archwire therein. The invalid pin pad intersection constraint 1974 evaluates the location of the locking pin on a bracket to ensure it does not protrude excessively into or through the front face of the pad.

The invalid slot depth constraint 1976 generally relates to evaluating the slot end faces to ensure they do not cut into the pad area of the bracket. When the slot is oriented too deep within either side of the bracket, the overall brace system is less efficient and generally not desired. Thus, the invalid slot depth constraint 1976 is found to be invalid when the slot encroaches too much into the ends of the bracket, based on a particular set threshold.

Figure 20:
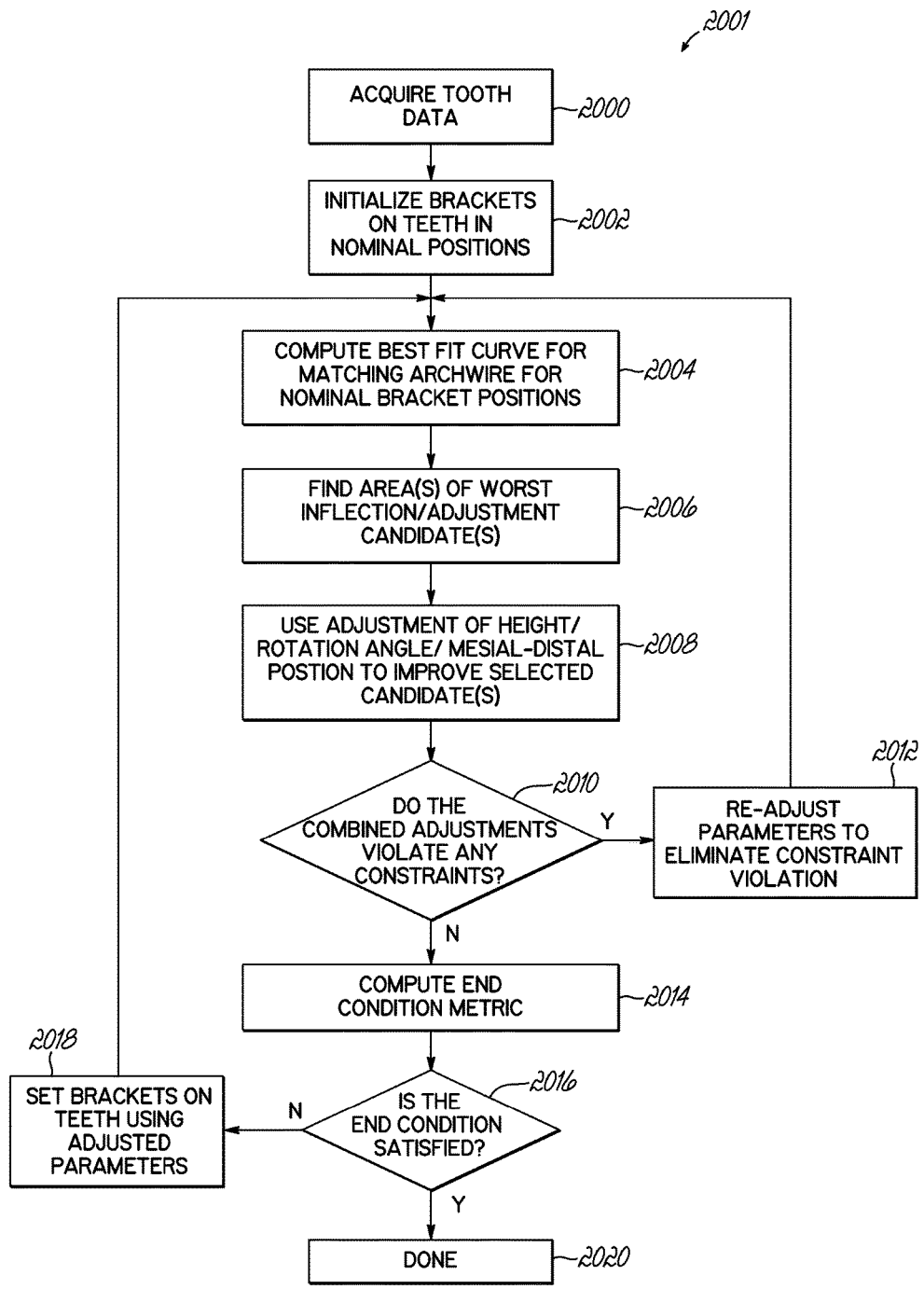
FIG. 20 illustrates a fourth flowchart that shows a process for adjusting the virtual brackets, in accordance with certain embodiments.

FIG. 20 illustrates a process or method of optimizing the placement of a set of orthodontic brackets using the aforementioned principles on a corresponding set of teeth, described hereafter as process 2001. As shown in a block 2000, initially, tooth data is acquired using some mechanism. The tooth data may be acquired through an intra-oral image scan of a patient's oral cavity, or a bite impression, or any other mechanism for acquiring a digital representation of a set of teeth. Inasmuch as process 2001 may require the tooth data in a particular format, the tooth data may be acquired in a required format or after acquisition, may be transformed or translated into a format required or preferred by process 2001. Once the tooth data is acquired, the data is passed on to a block 2002. In block 2002, a set of virtual brackets are initialized or positioned on the digital representation of the teeth in a nominal bracket position or layout.

After the brackets are initialized on the teeth in a nominal layout in block 2002, process 2001 proceeds to a block 2004, wherein a best fit curve for determining a path of a virtual archwire may be determined based on the placement of the brackets. Process 2001 may delineate the set of virtual brackets in the nominal bracket layout to determine the path of the virtual archwire. As shown in FIG. 19A, the path may be determined by deriving a vector for each tooth, whereby the vector is aligned with the two end points of the bracket. After the best fit curve for a matching archwire is determined in block 2004, process 2001 proceeds to a block 2006, wherein one or more brackets are determined to be adjustment candidates. The adjustment candidates may be the areas of worst inflection or may be determined by any other mechanism for selection of brackets for adjustment. After the adjustment candidates are selected, process 2001 proceeds to a block 2008.

In block 2008, the various parameters of the adjustment candidates are adjusted to re-position the at least one selected bracket on the corresponding tooth. This re-positioning transforms the nominal bracket layout into an updated bracket layout with the goal of smoothing the path of the archwire. After block 2008, process 2001 proceeds to a block 2010. In block 2010, a determination is made as to whether any of the adjustments or re-positioning of the brackets violate any constraints. If a constraint is violated, process 2001 proceeds to a block 2012. If the constraints are not violated, process 2001 proceeds to a block 2014. In block 2010, the adjustments are changed to prevent the violation of the constraint(s). Thereafter, process 2001 proceeds back to block 2004.

In block 2014, an end condition metric or termination criterion is computed. The end condition metric may be a tolerance or a threshold value based on a theoretical "perfect fit" of a set of virtual braces to the digital representation of the set of teeth 1906, or may be any other mechanism for use in determining whether process 2001 is complete. After the end condition metric is computed or updated in block 2014, process 2001 moves to a block 2016 whereby process 2001 determine whether the end condition metric satisfies an end condition. If the end condition is satisfied, process 2001 terminates in a block 2020. If the end condition is not satisfied, process 2001 proceeds to a block 2018.

Block 2018 sets the brackets on the teeth using the adjusted parameters and loops back to restart the re-positioning blocks, with the brackets already updated into a closer fit to the end condition metric. As such, the loop of blocks 2004, 2006, 2008, 2010, 2014, 2016, and 2018, work to iteratively adjust and re-position the brackets towards the optimal placement upon the set of teeth, without violating any of the constraints.

In an embodiment of the invention, blocks 2004, 2006, 2008, 2010, 2014, 2016, and 2018, or any combination of blocks illustrated in FIG. 20, may be logically combined and modeled mathematically as a constrained optimization problem to be solved using linear programming. The constrained optimization problem may include variables associated with the height parameter 1946, the rotation parameter 1948, and the medial-distal placement parameter 1950, as shown in FIG. 19G. Further, parameters such as those illustrated in FIG. 19H may be modeled mathematically as hard constraints within the constrained optimization problem.

Figure 21:
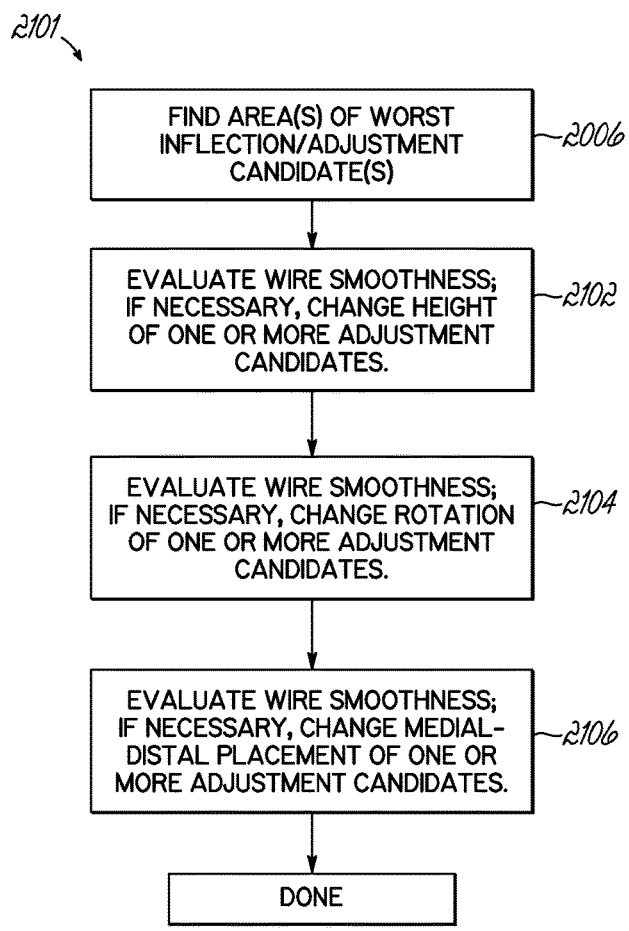
FIG. 21 illustrates a fifth flowchart that shows a process for adjusting the virtual brackets, in accordance with certain embodiments.

FIG. 21 illustrates a process or method of adjusting the position of the virtual brackets to smooth the archwire using the aforementioned principles, described hereafter as process 2101. Process 2101 may represent or may execute inside any one or more of the blocks of process 2001, shown in FIG. 20. In an embodiment of the invention, process 2101 is initiated by block 2006 of FIG. 20, wherein the areas of worst inflection and/or adjustment candidates are selected for adjustment.

Once the adjustment candidates are selected, process 2101 proceeds to a block 2102. In block 2102, process 2101 evaluates the smoothness of the wire proximate the selected adjustment candidates to determine if changing the height of one or more of the adjustment candidates will increase the smoothness of the archwire. As shown in FIG. 19G, in an embodiment of the invention, the height parameter 1946 of the virtual bracket data structure 1944 may be adjusted to facilitate the change in height of the underlying virtual bracket.

After the height related adjustments are made in block 2102, process 2101 proceeds to a block 2104. In block 2104, process 2101 evaluates the smoothness of the wire proximate the selected adjustment candidates to determine if changing the rotation of one or more of the adjustment candidates will increase the smoothness of the archwire. As shown in FIG. 19G, in an embodiment of the invention, the rotation parameter 1948 of the virtual bracket data structure 1944 may be adjusted to facilitate the change in rotation of the underlying virtual bracket.

After the rotation related adjustments are made in block 2104, process 2101 proceeds to a block 2106. In block 2106, process 2101 evaluates the smoothness of the wire proximate the selected adjustment candidates to determine if changing the medial-distal placement of one or more of the adjustment candidates will increase the smoothness of the archwire. As shown in FIG. 19G, in an embodiment of the invention, the medial-distal placement parameter 1950 of the virtual bracket data structure 1944 may be adjusted to facilitate the change in medial-distal placement of the underlying virtual bracket. The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method of optimizing a set of orthodontic brackets on a corresponding set of a patient's teeth, the method comprising:
   positioning a set of virtual brackets on a digital representation of the set of teeth in a nominal bracket layout, each virtual bracket including a slot;
   simulating an initial path of a virtual archwire through each slot in the set based on the nominal bracket layout;
   selecting at least two adjustment candidates based on the initial path, wherein each of the at least two adjustment candidates is one virtual bracket in the set of virtual brackets;
   modifying at least one of the adjustment candidates by at least one of changing a bracket height, changing an angle between the slot and a back surface of the virtual bracket, and rotating the slot in the virtual bracket about a centerline of the virtual bracket, wherein modifying updates the nominal bracket layout into an updated bracket layout;
   simulating an updated path of the virtual archwire through each slot in the updated bracket layout; and
   evaluating whether the updated bracket layout violates at least one constraint;
   in response to violation of the at least one constraint, repeating modifying the at least one adjustment candidate, simulating, and evaluating to produce another updated path;
   wherein modifying, simulating, and evaluating are performed one or more times to arrive at an updated bracket layout for manufacturing, the updated bracket layout satisfying the at least one constraint, and
   manufacturing the set of orthodontic brackets in accordance with the updated bracket layout.

2. The method of claim 1 wherein the at least one constraint includes a minimum bracket height, and wherein each virtual bracket in the set of virtual brackets is positioned at the minimum bracket height in the nominal bracket layout and in the updated bracket layout, the at least one adjustment candidate has a height greater than the minimum bracket height.

3. The method of claim 1 wherein each virtual bracket in the set of virtual brackets is positioned with the slot in a horizontal orientation in the nominal bracket layout and in the updated bracket layout, the slot of at least one virtual bracket is not oriented in the horizontal orientation.

4. The method of claim 1 wherein each virtual bracket in the set of virtual brackets is centered mesio-distally on a facial axis of a clinical crown (FACC) line of the associated tooth in the nominal bracket layout and in the updated bracket layout, at least one virtual bracket is offset from the FACC.

5. The method of claim 1 wherein each virtual bracket in the set of virtual brackets is associated with a height parameter, a rotation parameter, and a mesio-distal placement parameter, and wherein modifying the at least one adjustment candidate includes changing the height parameter, the rotation parameter, the mesio-distal placement parameter, or a combination thereof, of the at least one virtual bracket associated with the adjustment candidate.

6. The method of claim 1 wherein the at least one constraint is a minimum bracket height, a maximum bracket height, a maximum distance from a facial axis of a clinical crown (FACC) line, a maximum bracket rotation, a maximum slot rotation, or a combination thereof.

7. The method of claim 1 further comprising:
   determining an area of inflection on the initial path; and
   selecting the at least two adjustment candidates based at least in part on the area of inflection.

8. The method of claim 7 wherein the area of inflection is the area of greatest inflection along the initial path.

9. The method of claim 7 wherein determining the area of inflection includes constructing a force field and selecting the at least two adjustment candidates based on the force field, and modifying the at least one adjustment candidate to reduce the force field.

10. The method of claim 1 further comprising:
    delineating the set of virtual brackets in the nominal bracket layout to determine the initial path of the virtual archwire.

11. The method of claim 1 prior to selecting the at least two adjustment candidates, the method further comprises:
    determining a desired path for the virtual archwire based on the set of teeth;

comparing the desired path and the initial path; and selecting the adjustment candidate based on the comparison of the desired path and the initial path.

12. The method of claim 1 wherein the manufacturing step further comprises:

generating a set of machine codes based on the updated bracket layout;

communicating the set of machine codes to a bracket manufacturing machine; and fabricating the set of orthodontic brackets by the bracket manufacturing machine based on the machine codes.

13. The method of claim 1 further comprising:

acquiring the digital representation of the set of teeth through intra-oral imaging.

14. The method of claim 1 wherein modifying the at least one of the adjustment candidates includes integrating first order derivatives over a curve defined by the initial path, integrating second order derivatives of the curve, and minimizing a sum of the integrated first order derivatives and integrated second order derivatives.

15. A method of optimizing a set of orthodontic brackets on a corresponding set of teeth, the method comprising:

positioning a set of virtual brackets on a digital representation of the set of teeth in a nominal bracket layout;

iteratively, until an archwire smoothness is met:

simulating a path of a virtual archwire based on the bracket layout;

based on the path, selecting at least one virtual bracket in the set of virtual brackets for adjustment;

modifying a dimension of the selected at least one virtual bracket in accordance with at least one constraint, wherein modifying updates the bracket layout; and determining whether the archwire smoothness is met; and manufacturing the set of orthodontic brackets in accordance with the updated bracket layout.

16. The method of claim 15 wherein the at least one constraint includes a minimum bracket height, and wherein each virtual bracket in the set of virtual brackets is positioned at the minimum bracket height in the nominal bracket layout and changing the dimension increases the bracket height from the minimum bracket height when the archwire smoothness is met.

17. The method of claim 15 wherein each virtual bracket in the set of virtual brackets includes a slot having an orientation, and wherein each virtual bracket in the set of virtual brackets is positioned with the slot in a horizontal orientation in the nominal bracket layout and changing the dimension orients the slot in an orientation other than the horizontal orientation when the archwire smoothness is met.

18. The method of claim 15 wherein each virtual bracket in the set of virtual brackets is centered mesio-distally on a facial axis of a clinical crown (FACC) of the associated tooth in the nominal bracket layout and changing the dimension includes moving the virtual bracket away from the FACC when the archwire smoothness is met.

19. The method of claim 15 wherein the dimension is associated with a height parameter, a rotation parameter, and a mesio-distal placement parameter, and wherein modifying the dimension includes changing the height parameter, the rotation parameter, the mesio-distal placement parameter, or a combination thereof, of the at least one virtual bracket when the archwire smoothness is met.

20. The method of claim 15 wherein following selecting the path, the method further comprises at least one of:

integrating first order derivatives over a curve defined by the path, integrating second order derivatives of the curve, and minimizing a sum of the integrated first order derivatives and integrated second order derivatives during modifying the dimension; or constructing a force field, determining an area of inflection on the path based on the force field, and modifying the dimension based on the area of inflection.

21. The method of claim 15 further comprising:

determining a desired path for the virtual archwire based on the set of teeth;

comparing the desired path and the simulated path from the simulating step; and selecting the at least one virtual bracket based on the comparison of the desired path and the simulated path.

22. A system comprising:

a brace designing application residing in a memory of a computer system, wherein the brace designing application is configured to accept a digital representation of a set of teeth from an intra-oral imaging device or an impression scanning device;

the brace designing application further configured to position a set of virtual brackets on the digital representation of the set of teeth in a nominal bracket layout and iteratively, until an archwire smoothness is met:

simulate a path of a virtual archwire based on the bracket layout;

based on the path, select at least one virtual bracket in the set of virtual brackets for adjustment;

modifying a dimension of the selected at least one virtual bracket in accordance with at least one constraint, wherein modifying updates the bracket layout; and determine whether the archwire smoothness is met; and a bracket manufacturing machine configured to manufacture a set of orthodontic brackets in accordance with the updated bracket layout when the archwire smoothness is met.

* * * * *